US012350660B2

(12) United States Patent
Holtz et al.

(10) Patent No.: US 12,350,660 B2
(45) Date of Patent: Jul. 8, 2025

(54) MODULAR, SELF-CONTAINED, MOBILE CLEAN ROOM

(71) Applicant: G-CON Manufacturing, Inc., College Station, TX (US)

(72) Inventors: R. Barry Holtz, Houston, TX (US); Troy Arledge, Rockdale, TX (US); Phillip B. Maples, Pilot Point, TX (US); David M. Shanahan, Dallas, TX (US)

(73) Assignee: G-CON Manufacturing, Inc., College Station, TX (US)

(*) Notice: Subject to any disclaimer, the term of this patent is extended or adjusted under 35 U.S.C. 154(b) by 115 days.

(21) Appl. No.: 16/854,752

(22) Filed: Apr. 21, 2020

(65) Prior Publication Data

US 2020/0246787 A1 Aug. 6, 2020

Related U.S. Application Data

(60) Division of application No. 15/727,002, filed on Oct. 6, 2017, now Pat. No. 10,654,036, which is a division
(Continued)

(51) Int. Cl.
*C12M 1/12* (2006.01)
*B01L 1/04* (2006.01)
(Continued)

(52) U.S. Cl.
CPC ............... *B01L 1/04* (2013.01); *B23P 11/00* (2013.01); *C12M 37/00* (2013.01); *F24F 3/167* (2021.01); *Y02A 50/20* (2018.01); *Y10T 29/49826* (2015.01)

(58) Field of Classification Search
CPC ........... B01L 1/04; B23P 11/00; C12M 37/00; Y02A 50/20; Y10T 29/49826
See application file for complete search history.

(56) References Cited

U.S. PATENT DOCUMENTS 1,967,511 A 7/1934 Meyer
1,991,536 A 2/1935 Austin
(Continued)

FOREIGN PATENT DOCUMENTS

CN 1373824 A 10/2002
CN 2012/81413 Y 7/2009
(Continued)

OTHER PUBLICATIONS

Translation of JP-2007198666-A (Year: 2007).*
(Continued)

*Primary Examiner* — Steven S Anderson, II
(74) *Attorney, Agent, or Firm* — Mark P. Mathison

(57) ABSTRACT

Biosafety units, methods of making and sealing the same are disclosed herein. The present invention includes a unitary structure able to be validated for pharmaceutical manufacturing comprising: at least one controlled air, sealable, sterilizable cleanroom; a mechanical system room adjacent to and separate from the cleanroom comprising: one or more air handling units that provide conditioned air to the cleanroom; and one or more power busses that provide power to electrical outlets in the cleanroom from two sources, wherein the at least two power supplies are connectable to one or more external electrical power sources; an integrated fire suppression system integral to the cleanroom; and one or more corridor connectors, wherein a corridor can be attached at the corridor connector.

12 Claims, 17 Drawing Sheets

Related U.S. Application Data of application No. 13/669,785, filed on Nov. 6, 2012, now Pat. No. 9,795,957, which is a continuation-in-part of application No. 12/856,888, filed on Aug. 16, 2010, now Pat. No. 9,518,748.

(60) Provisional application No. 61/234,302, filed on Aug. 16, 2009.

(51) Int. Cl.
| | | |
|---|---|---|
| *B23P 11/00* | (2006.01) | |
| *E04H 3/08* | (2006.01) | |
| *E04H 5/02* | (2006.01) | |
| *F24F 3/167* | (2021.01) | |

(56) References Cited

U.S. PATENT DOCUMENTS

| | | | |
|---|---|---|---|
| 2,156,859 A | 5/1937 | Lowe | |
| 2,098,111 A | 11/1937 | Sconce | |
| 2,168,725 A | 8/1939 | Whelan | |
| 3,115,819 A | 12/1963 | Mahlmeister | |
| 3,378,963 A | 4/1968 | Obata | |
| 3,456,829 A | 7/1969 | Glassmeyer | |
| 3,470,871 A | 10/1969 | Shoen | |
| 3,540,173 A * | 11/1970 | Johnides | E04H 3/08 |
| | | | 52/79.5 |
| 3,570,385 A | 3/1971 | Heisterkamp et al. | |
| 3,623,283 A | 11/1971 | Abromavage et al. | |
| 3,638,404 A | 2/1972 | Moll et al. | |
| 3,638,641 A | 2/1972 | Abromavage et al. | |
| 3,678,639 A | 7/1972 | Panitz | |
| 3,742,932 A | 7/1973 | Greenspan | |
| 3,756,342 A | 9/1973 | Burdick | |
| 3,766,844 A | 10/1973 | Donnelly | |
| 4,255,912 A | 3/1981 | Kovacs | |
| 4,267,769 A | 5/1981 | Davis et al. | |
| 4,304,224 A | 12/1981 | Fortney | |
| 4,327,529 A | 5/1982 | Bigelow et al. | |
| 4,409,889 A * | 10/1983 | Burleson | F24F 3/167 |
| | | | 55/385.2 |
| 4,549,472 A | 10/1985 | Endo et al. | |
| 4,554,766 A | 11/1985 | Ziemer et al. | |
| 4,599,829 A | 7/1986 | DiMartino, Sr. | |
| 4,667,579 A | 5/1987 | Daw | |
| 4,667,580 A | 5/1987 | Wetzel | |
| 4,682,418 A | 7/1987 | Tuss et al. | |
| 4,693,175 A | 9/1987 | Hashimoto | |
| 4,694,736 A | 9/1987 | Yamagata | |
| 4,731,961 A | 3/1988 | Bona | |
| 4,820,931 A | 4/1989 | Dunbar | |
| 4,850,268 A | 7/1989 | Saito et al. | |
| 4,860,420 A | 8/1989 | Cadwell et al. | |
| 4,869,156 A | 9/1989 | Hutton | |
| 4,883,512 A | 11/1989 | Griffis | |
| 4,923,352 A | 5/1990 | Tamura et al. | |
| 5,029,518 A | 7/1991 | Austin | |
| 5,058,491 A | 10/1991 | Wiemer et al. | |
| 5,096,477 A | 3/1992 | Shinoda et al. | |
| 5,125,203 A | 6/1992 | Daw | |
| 5,128,855 A | 7/1992 | Hilber | |
| 5,152,814 A | 10/1992 | Nelson | |
| 5,163,517 A | 11/1992 | Kozai et al. | |
| 5,195,922 A | 3/1993 | Genco | |
| 5,207,035 A | 5/1993 | Fowler | |
| 5,256,105 A | 10/1993 | Austin | |
| 5,259,812 A * | 11/1993 | Kleinsek | F24F 3/167 |
| | | | 312/1 |
| 5,279,632 A | 1/1994 | Decker et al. | |
| 5,326,316 A | 7/1994 | Hashimoto et al. | |
| 5,344,365 A | 9/1994 | Scott et al. | |
| 5,350,336 A | 9/1994 | Chen et al. | |
| 5,474,411 A | 12/1995 | Schoenfeld et al. | |
| 5,511,594 A * | 4/1996 | Brennan | A61J 3/00 |
| | | | 53/425 |
| 5,562,539 A | 10/1996 | Hashimoto et al. | |
| 5,626,786 A | 5/1997 | Huntington et al. | |
| 5,641,354 A | 6/1997 | Sakauchi | |
| 5,656,491 A | 8/1997 | Cassani et al. | |
| 5,706,846 A | 1/1998 | Sutton | |
| 5,713,791 A | 2/1998 | Long et al. | |
| 5,735,639 A | 4/1998 | Payne et al. | |
| 5,752,985 A | 5/1998 | Nagafune et al. | |
| 5,795,356 A | 8/1998 | Leveen | |
| 5,941,846 A | 8/1999 | Duffy et al. | |
| 6,044,596 A | 4/2000 | Driggett | |
| 6,132,309 A | 10/2000 | Panelli et al. | |
| 6,179,358 B1 | 1/2001 | Hirayama et al. | |
| 6,179,522 B1 | 1/2001 | Sanford et al. | |
| 6,196,514 B1 | 3/2001 | Kienholz | |
| 6,304,005 B1 | 10/2001 | Aoki et al. | |
| 6,360,494 B1 | 3/2002 | Emerson | |
| 6,394,523 B1 | 5/2002 | Yoo et al. | |
| 6,397,755 B1 | 6/2002 | Kamler | |
| 6,450,411 B1 | 9/2002 | Rash et al. | |
| 6,512,384 B1 | 1/2003 | Lagowski et al. | |
| 6,602,128 B1 | 8/2003 | Spengler | |
| 6,602,457 B1 | 8/2003 | Lee et al. | |
| 6,634,149 B2 | 10/2003 | Cates et al. | |
| 6,688,055 B2 | 2/2004 | Lindsley | |
| 6,869,457 B2 | 3/2005 | Nakagawa | |
| 6,925,761 B1 | 8/2005 | De La Marche | |
| 6,960,236 B1 | 11/2005 | Tamura et al. | |
| 6,969,102 B2 | 11/2005 | Orischak et al. | |
| 7,022,009 B2 | 4/2006 | Kim | |
| 7,083,515 B2 | 8/2006 | Rapisarda et al. | |
| 7,160,717 B2 | 1/2007 | Everett | |
| 7,162,833 B2 | 1/2007 | Faris | |
| 7,222,246 B2 | 5/2007 | Pomaranski et al. | |
| 7,272,733 B2 | 9/2007 | Pomaranski et al. | |
| 7,323,025 B2 | 1/2008 | Weidner | |
| 7,326,355 B2 | 2/2008 | Graetz et al. | |
| 7,472,513 B2 | 1/2009 | Bula | |
| 7,511,960 B2 | 3/2009 | Hillis et al. | |
| 7,527,664 B2 | 5/2009 | Jackson | |
| 7,586,420 B2 | 9/2009 | Fischer et al. | |
| 7,707,931 B2 | 5/2010 | Garrett et al. | |
| 7,724,513 B2 | 5/2010 | Coglitore et al. | |
| 7,827,738 B2 | 11/2010 | Abrams et al. | |
| 7,861,102 B1 | 12/2010 | Ranganathan et al. | |
| 7,934,124 B2 | 4/2011 | Bechtolsheim et al. | |
| 7,985,382 B1 * | 7/2011 | Henry | E04H 1/1277 |
| | | | 422/291 |
| 8,001,730 B2 | 8/2011 | Wallance | |
| 8,061,080 B2 | 11/2011 | Loebl et al. | |
| 8,065,560 B1 | 11/2011 | Patil | |
| 8,147,301 B2 | 4/2012 | Ghattas | |
| 8,239,340 B2 | 8/2012 | Hanson | |
| 8,322,086 B2 | 12/2012 | Weber | |
| 8,371,912 B2 | 2/2013 | Ozeki | |
| 8,397,441 B2 | 3/2013 | Wallance | |
| 8,479,038 B1 | 7/2013 | Patil | |
| 8,584,349 B2 | 11/2013 | Scannon et al. | |
| 8,656,670 B2 | 2/2014 | Mouzannar | |
| 8,826,600 B2 | 9/2014 | Wallance | |
| 8,854,349 B2 | 10/2014 | Eom et al. | |
| 9,115,504 B2 | 8/2015 | Wallance | |
| 9,187,894 B2 | 11/2015 | Zadok et al. | |
| 9,353,543 B2 | 5/2016 | Lam | |
| 9,518,748 B2 | 12/2016 | Holtz et al. | |
| 9,671,798 B2 | 6/2017 | Hodge et al. | |
| 9,765,980 B2 | 9/2017 | Holtz et al. | |
| 9,795,957 B2 | 10/2017 | Holtz et al. | |
| 10,006,218 B2 | 6/2018 | Marinoni | |
| 10,161,147 B2 | 12/2018 | Jornitz | |
| 10,371,394 B2 | 8/2019 | Wernimont et al. | |
| 10,371,411 B2 | 8/2019 | Cursetjee et al. | |
| 10,654,036 B2 | 5/2020 | Holtz et al. | |
| 2002/0174888 A1 | 11/2002 | Brown | |
| 2003/0045226 A1 | 3/2003 | Yokoyama et al. | |
| 2003/0140555 A1 | 7/2003 | Saether | |
| 2004/0159051 A1 | 8/2004 | Lam | |
| 2004/0194484 A1 | 10/2004 | Zou et al. | |
| 2005/0082445 A1 | 4/2005 | Groves | |

(56) References Cited

U.S. PATENT DOCUMENTS

| | | |
|---|---|---|
| 2005/0091916 A1 | 5/2005 | Faris |
| 2005/0124010 A1 | 6/2005 | Short et al. |
| 2005/0154494 A1 | 7/2005 | Ahmed |
| 2005/0193643 A1 | 9/2005 | Pettus |
| 2006/0107635 A1 | 5/2006 | Homan et al. |
| 2006/0217056 A1 | 9/2006 | Gomi et al. |
| 2006/0234621 A1 | 10/2006 | Desrochers |
| 2007/0039260 A1 | 2/2007 | Haddad |
| 2007/0089854 A1 | 4/2007 | Jaisinghani |
| 2007/0130844 A1 | 6/2007 | Arts et al. |
| 2007/0132262 A1 | 6/2007 | Chui Peng Sun et al. |
| 2007/0167126 A1 | 7/2007 | Ghattas |
| 2007/0228692 A1 | 10/2007 | Kern et al. |
| 2007/0251145 A1 | 11/2007 | Brusatore |
| 2007/0253831 A1 | 11/2007 | Lee |
| 2008/0005976 A1 | 1/2008 | Montaigne |
| 2008/0047207 A1 | 2/2008 | Lam |
| 2008/0047224 A1 | 2/2008 | Lam |
| 2008/0086980 A1 | 4/2008 | Martin |
| 2008/0201008 A1 | 8/2008 | Twelves et al. |
| 2008/0302004 A1 | 12/2008 | Lin |
| 2009/0122533 A1 | 5/2009 | Brukilacchio |
| 2009/0126285 A1 | 5/2009 | Suh |
| 2009/0199470 A1 | 8/2009 | Capen et al. |
| 2009/0305626 A1 | 12/2009 | Hope |
| 2010/0031564 A1 | 2/2010 | Loebl et al. |
| 2010/0112677 A1 | 5/2010 | Onishi et al. |
| 2010/0112926 A1 | 5/2010 | Ozeki |
| 2010/0192493 A1 | 8/2010 | Nakai |
| 2010/0251677 A1 | 10/2010 | Franck |
| 2010/0304658 A1 | 12/2010 | Grcevic |
| 2011/0053486 A1 | 3/2011 | Holtz et al. |
| 2011/0217917 A1 | 9/2011 | Sulva |
| 2011/0219953 A1 | 9/2011 | Schreiber |
| 2011/0258837 A1 | 10/2011 | Scannon et al. |
| 2012/0077429 A1 | 3/2012 | Wernimont et al. |
| 2012/0099035 A1 | 4/2012 | Burgess |
| 2012/0152800 A1 | 6/2012 | Parzy et al. |
| 2012/0181869 A1 | 7/2012 | Chapel et al. |
| 2013/0109291 A1 | 5/2013 | Holtz et al. |
| 2014/0179216 A1 | 6/2014 | Walters |
| 2015/0101264 A1 | 4/2015 | Jornitz |
| 2015/0101265 A1 | 4/2015 | Nyce et al. |
| 2015/0159127 A1 | 6/2015 | Guerini et al. |
| 2016/0010883 A1 | 1/2016 | Jornitz et al. |
| 2016/0010884 A1 | 1/2016 | Holtz et al. |
| 2017/0030097 A1 | 2/2017 | Marinoni |
| 2017/0260763 A1 | 9/2017 | Fortin et al. |
| 2018/0043347 A1 | 2/2018 | Holtz et al. |
| 2019/0145118 A1 | 5/2019 | Gauthier et al. |
| 2020/0146186 A1 | 5/2020 | Fotouh |

FOREIGN PATENT DOCUMENTS

| | | |
|---|---|---|
| CN | 101501180 | 8/2009 |
| CN | 102884256 A | 1/2013 |
| CN | 105723036 A | 6/2016 |
| CN | 107002408 A | 8/2017 |
| CN | 107371371 A | 11/2017 |
| CN | 108884673 A | 11/2018 |
| DE | 8913876 U1 | 1/1990 |
| DE | 4007740 A1 | 9/1991 |
| EP | 940292 A2 | 9/1999 |
| EP | 2098111 A1 | 9/2009 |
| EP | 3263789 | 1/2018 |
| EP | 3274524 | 1/2018 |
| FR | 2819536 A1 | 7/2002 |
| JP | 61101733 | 5/1986 |
| JP | 62130331 | 8/1987 |
| JP | H09296944 A * | 11/1987 |
| JP | 6456812 | 4/1989 |
| JP | 2209526 A | 8/1990 |
| JP | H06174279 A | 6/1994 |
| JP | D6183511 | 7/1994 |
| JP | 2627041 | 7/1997 |
| JP | 10077711 | 3/1998 |
| JP | 11166269 A | 6/1999 |
| JP | 200054654 A | 2/2000 |
| JP | 2000/142211 A | 5/2000 |
| JP | 2001/141274 A | 5/2001 |
| JP | 2002221464 | 8/2002 |
| JP | 2004033498 | 5/2004 |
| JP | 20044233021 | 8/2004 |
| JP | 2007107779 | 4/2007 |
| JP | 2007107830 | 4/2007 |
| JP | 2007198666 A * | 8/2007 |
| JP | 2008139777 | 6/2008 |
| JP | 2008161114 | 7/2008 |
| JP | 2008/304989 A | 12/2008 |
| JP | 2009/002634 A | 1/2009 |
| JP | 6117169 | 3/2017 |
| KR | 100675682 | 12/2006 |
| KR | 20060130383 | 12/2006 |
| TW | 200912219 A | 3/2009 |
| WO | 2000/02618 A1 | 1/2000 |
| WO | 0017462 A1 | 3/2000 |
| WO | 2003/095765 A1 | 11/2003 |
| WO | 2004/005170 A1 | 1/2004 |
| WO | 2003/095765 A2 | 6/2007 |
| WO | 2007/067656 A2 | 6/2007 |
| WO | 2008/018671 A1 | 2/2008 |
| WO | 2011022325 A2 | 2/2011 |
| WO | 2013/132086 A1 | 12/2013 |
| WO | 2018006184 A1 | 1/2018 |

OTHER PUBLICATIONS

American Solving, Floor Specifications, http://www.solvinginc.com/floor_specifications.htm (Year: 2008).*
"Fast-track clean room building," European Semiconductor, UK, Mar. 1992, vol. 14, No. 3, pp. 43, 45.
Anonymous, "Clean-room products and equipment," Medical Device Technology, Chester, Jan./Feb. 2005, vol. 16, pp. 43-44. Document URL: http://search.proquest.com/docview/195254246?accountid=142944.
Astra-Zeneca Pharmaceutical Building, "Vanguard Modular Building Systems Brochure," Dec. 9, 2004, 2 pages.
Hovair Systems, Pneumatic Powered Load Moving Systems—Air Bering Principle, https://webarchive.org/web/20080521025052/http://www.hovair.com/air-bearing-info/features-and-benefits.htm, May 21, 2008.
Muth, Laboratory Design, "Modular Construction: Pros and Cons for the Lab Building," R&D Magazine, Jun. 17, 2009, 5 pages.
Oliviera, Tony, "Factory in a Clean Room," Quality Progress, Milwaukee, Jan. 1990, vol. 23, No. 1, p. 37. Document URL: http://search.proquest.com/docview/214764942?accountid=142944.
Pharmadule Press Release "Pharmadule Doubles Production Capacity and Acquires Patent for Modular Biotech Plants," Sep. 27, 2002, 1 page, http://www.pharmadule.com/pharmadule-doubles-production-capacity.
Watkins, B., "Clean rooms: their performance and design," Journal of Semi-Custom ICs, UK, Mar. 1985, vol. 2, No. 3, pp. 36-40.
EP10810440.7 , "Extended European Search Report", Apr. 22, 2014, 6 pages.
Hines , "A&M—Affiliated Company Could be Tasked With Ebola-Drug Production", Houston Chronicle, Available Online at http://www.houstonchronicle.com/business/medical/article/A-M-affiliatedcompany-could-be-tasked-with-5815166.php, Oct. 12, 2014, 2 pages.
Moore , "Texas Biotech Firm Affirms Readiness to Produce Commercial Quantities of Anti-Ebola Vaccines and Biotherapeutics Quickly and Cost-Effectively If Asked", BioNews-TX, Available Online at http://bionews-tx.com/news/2014/08/08/texas-biotech-firm-affirmsreadiness-produce-commercial-quantities-anti-ebola-vaccinesbiotherapeutics-quickly-cost-effectively-asked/, Aug. 8, 2014.
PCT/US2010/045599 , "International Preliminary Report on Patentability", Mar. 1, 2012, 6 pages.

(56) References Cited

OTHER PUBLICATIONS

PCT/US2010/045599, "International Search Report and Written Opinion", Feb. 8, 2011, 7 pages.
PCT/US2020/046143, "International Search Report and Written Opinion", Dec. 2, 2020, 10 pages.
Pollack, "Ebola Therapy From an Obscure Biotech Firm Is Hurried Along", The New York Times, Available Online at https://www.nytimes.com/2014/08/07/business/an-obscure-biotech-firm-hurries-ebola-treatment.html#:~:text=Inside%20special%20isolation%20units%20at,ties%20to%20the%20Defense%20Department, Aug. 6, 2014, 6 pages.
Stanton, "G-CON's Containment PODs Launched in Response to Ebola Crisis", Available Online at BioPharma-Reporter.com, Aug. 19, 2014, 2 pages.
PCT/US2021/046271, "International Search Report and Written Opinion", Nov. 29, 2021, 10 pages.
"Hardwall Cleanroom", HDW Series, Abtech Incorporated, Accessed from Internet on: Sep. 3, 2020, pp. 8.
"Starrco Brochure", Cleanroom Solutions, Accessed from Internet on: Sep. 3, 2020, 4 pages.
PCT/US2020/046143, "International Preliminary Report on Patentability", Feb. 24, 2022, 8 pages.
PCT/US2021/046271, "International Preliminary Report on Patentability", Mar. 9, 2023, 7 pages.

\* cited by examiner

| FIG. 9A-1 | FIG. 9A-2 |
|---|---|
| FIG. 9A-3 | FIG. 9A-4 |

FIG. 9A

| FIG. 5-1 | FIG. 5-2 |
|---|---|
| FIG. 5-3 | FIG. 5-4 |

FIG. 5

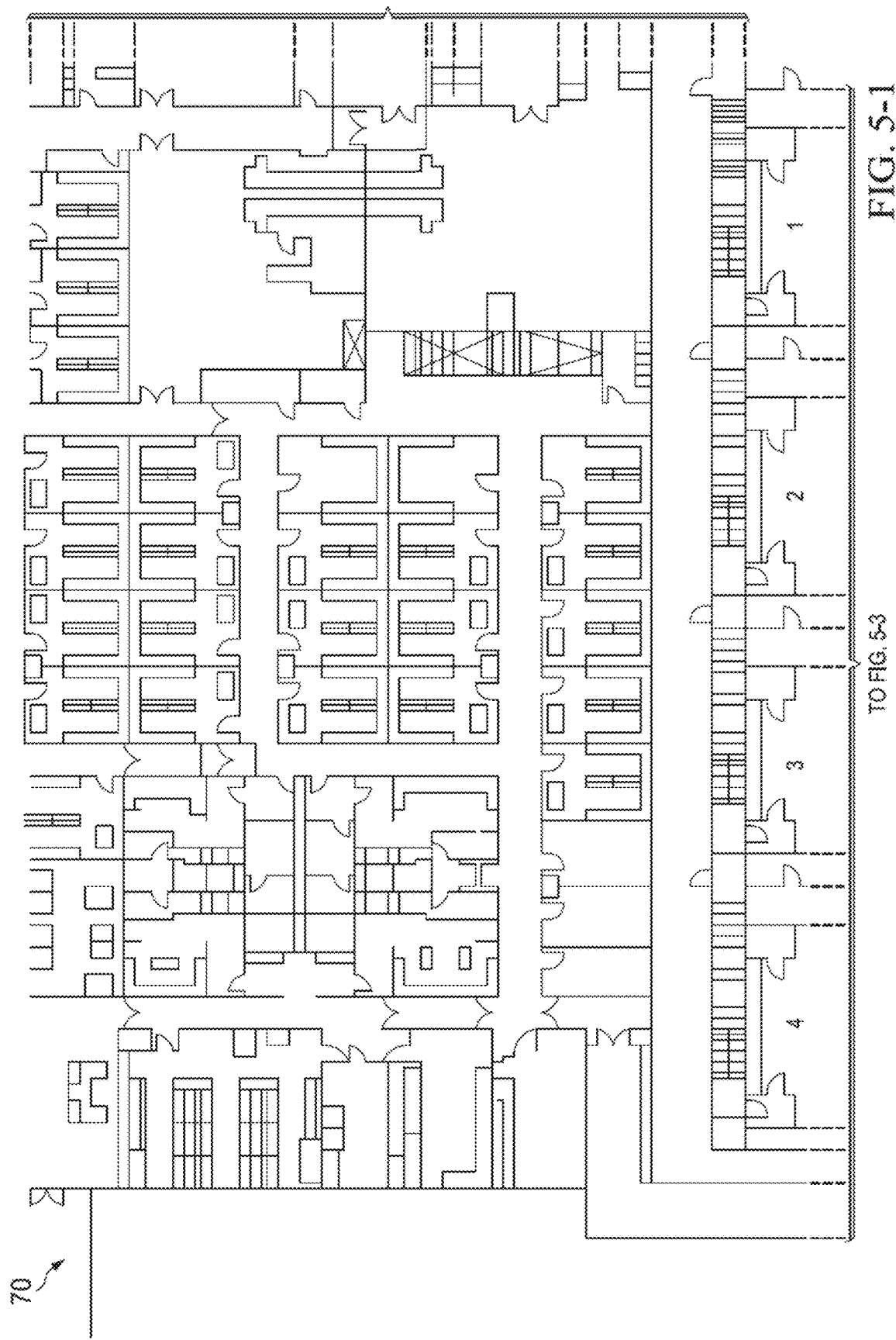

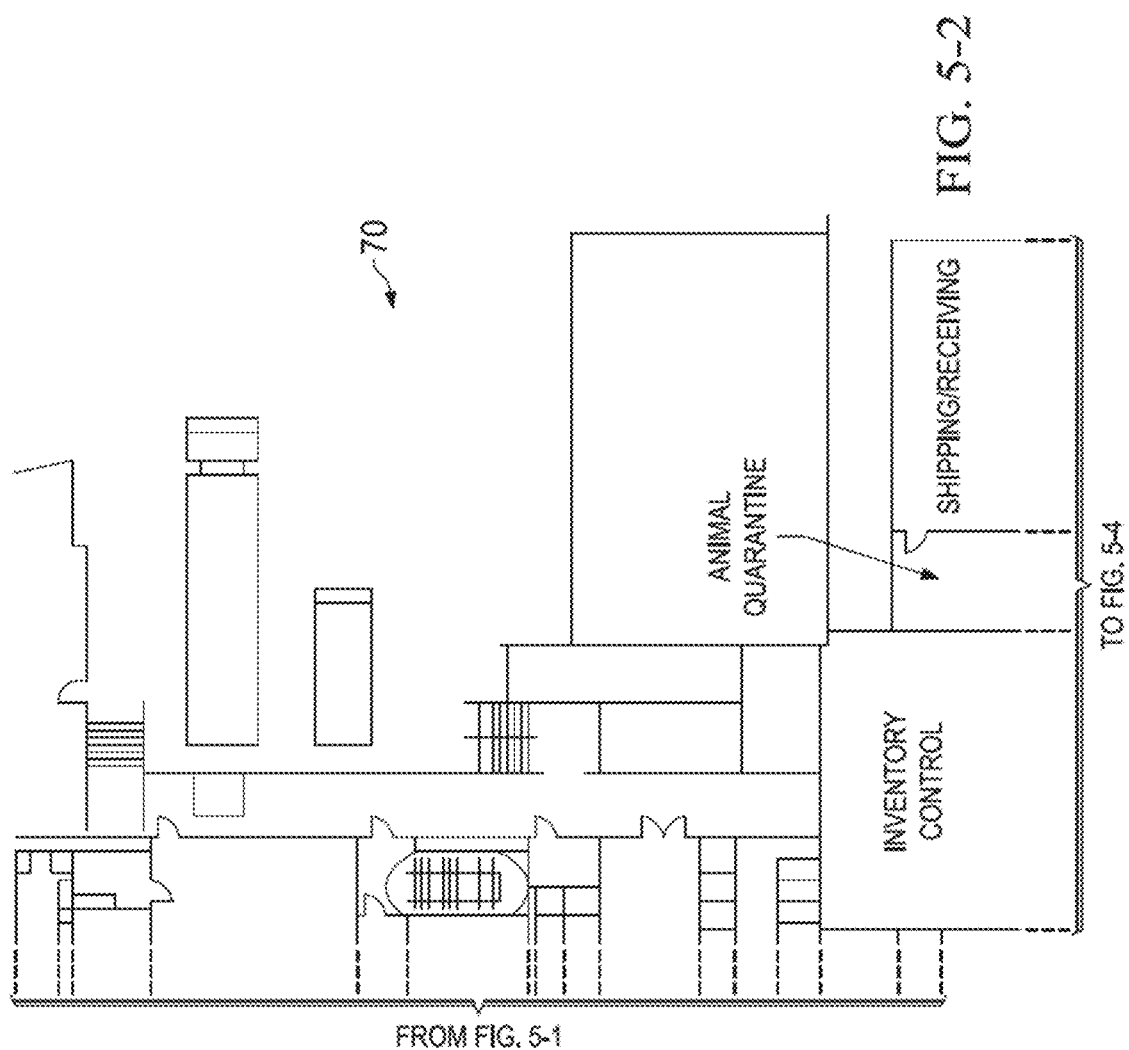

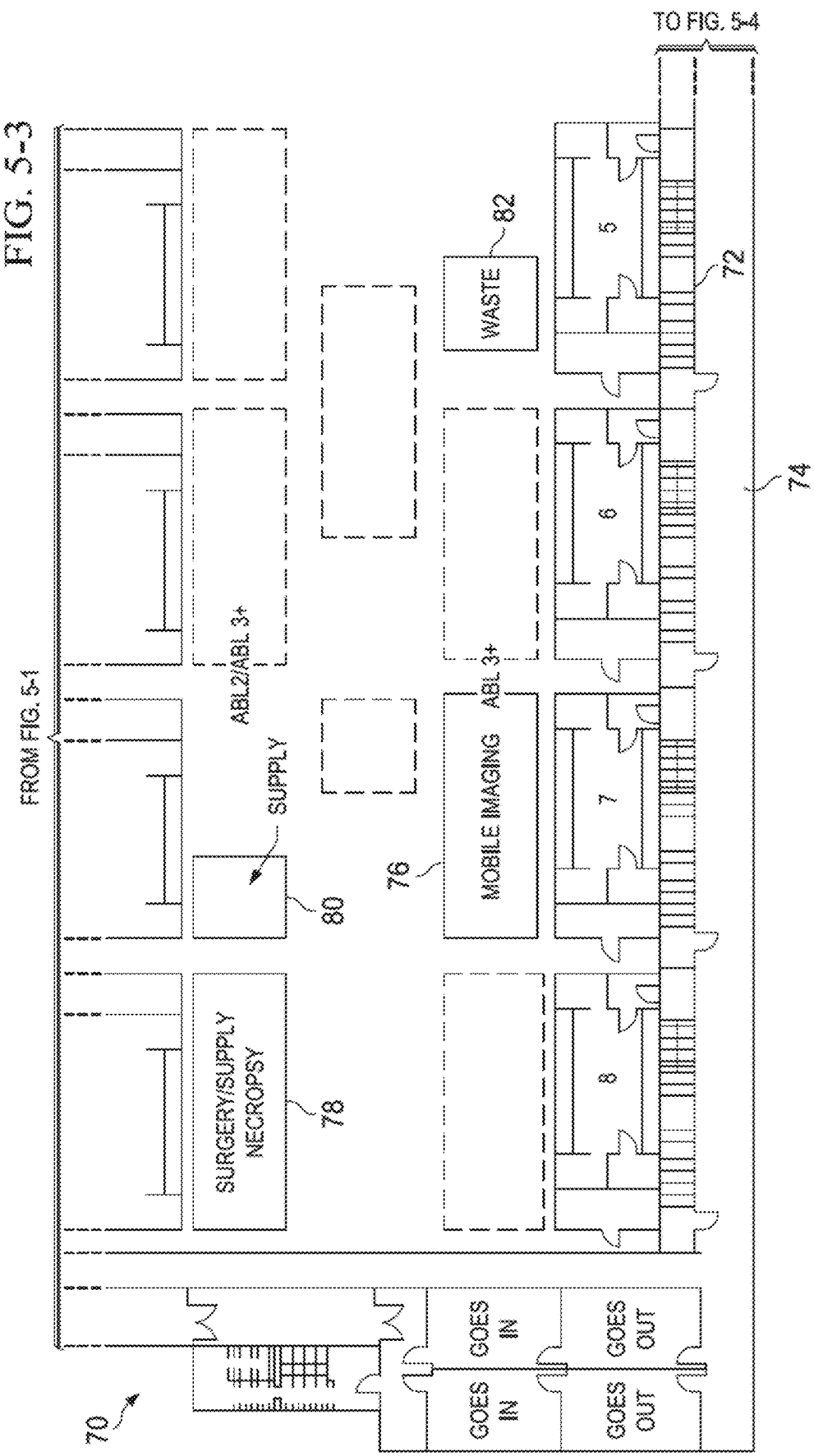

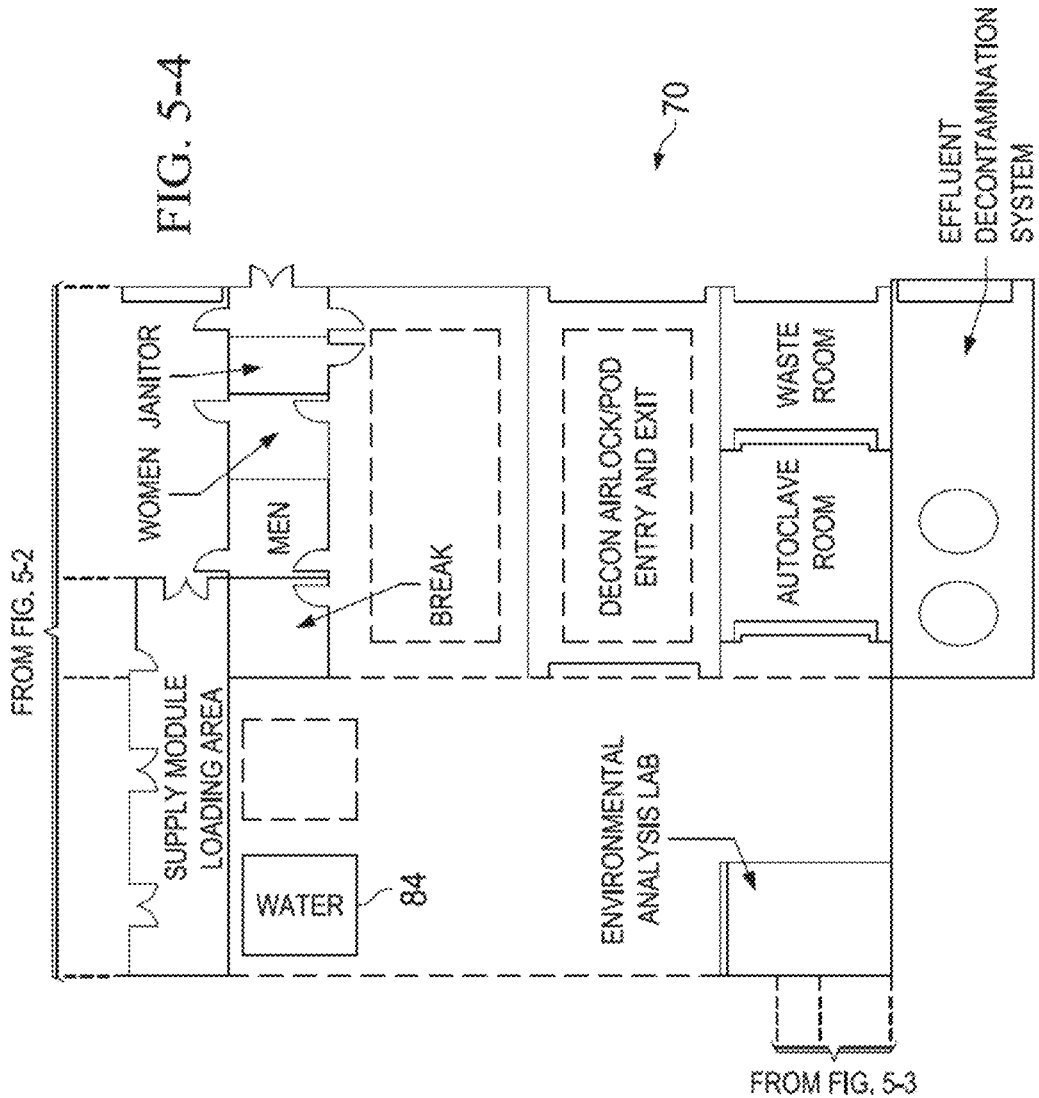

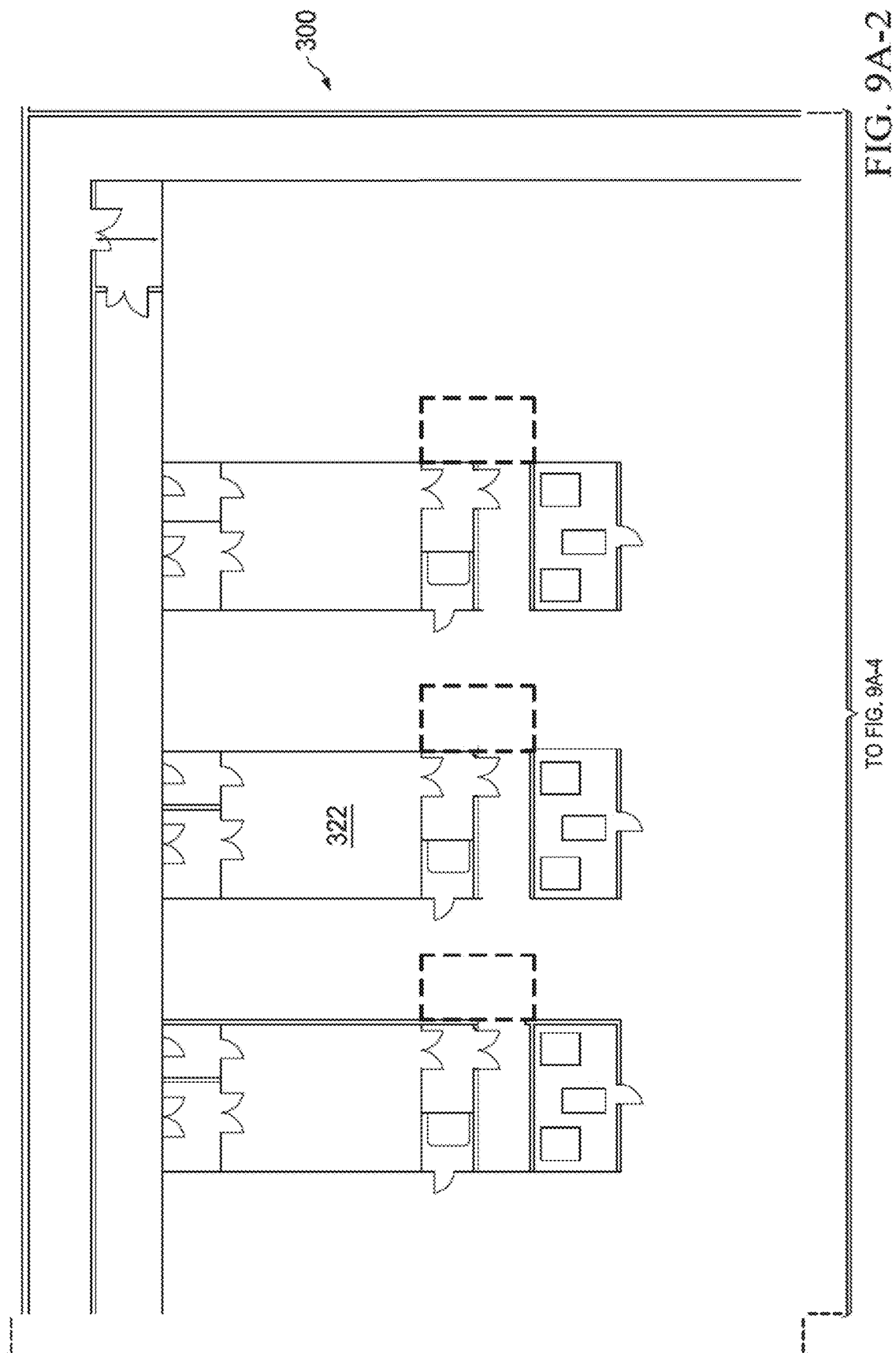

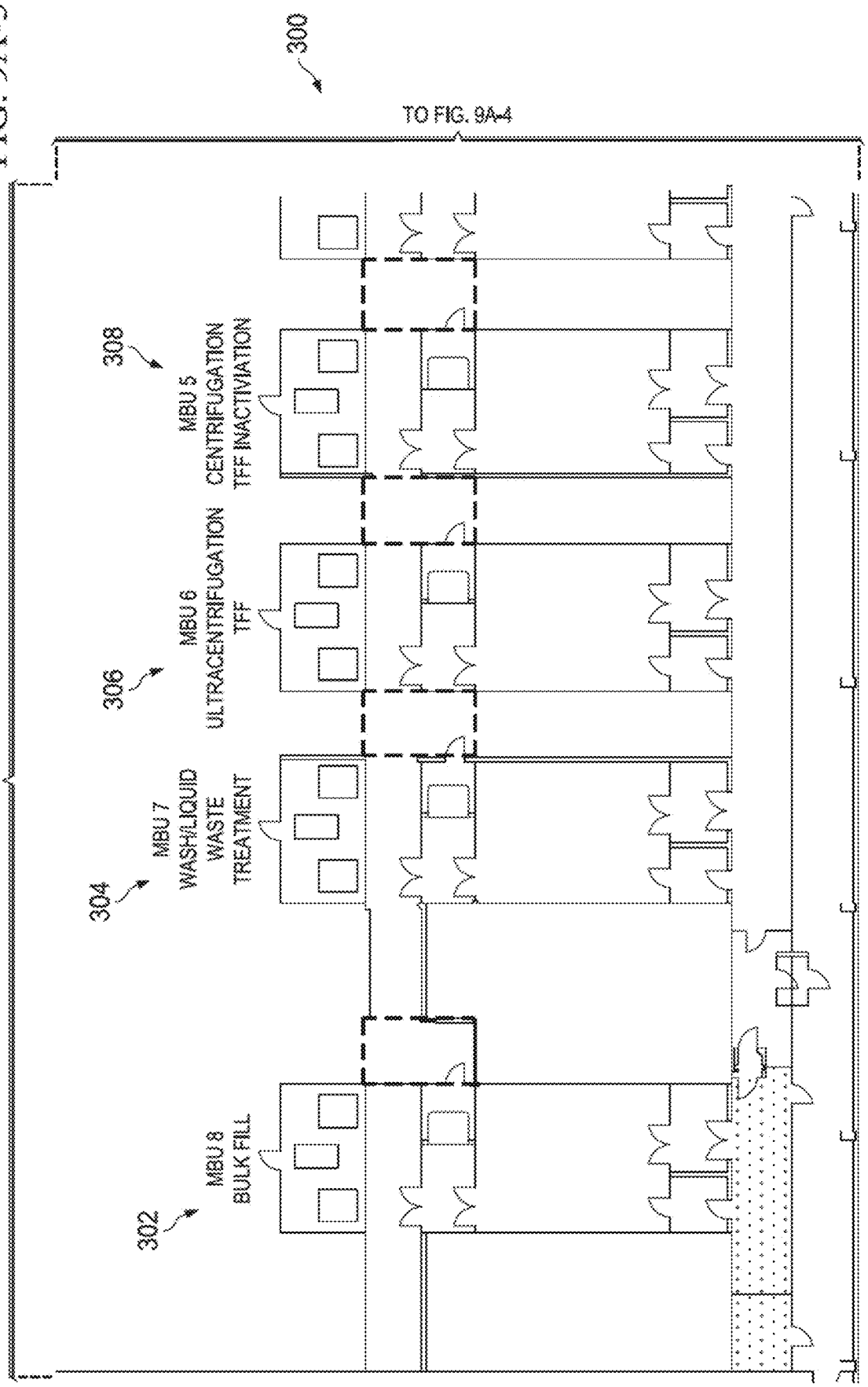

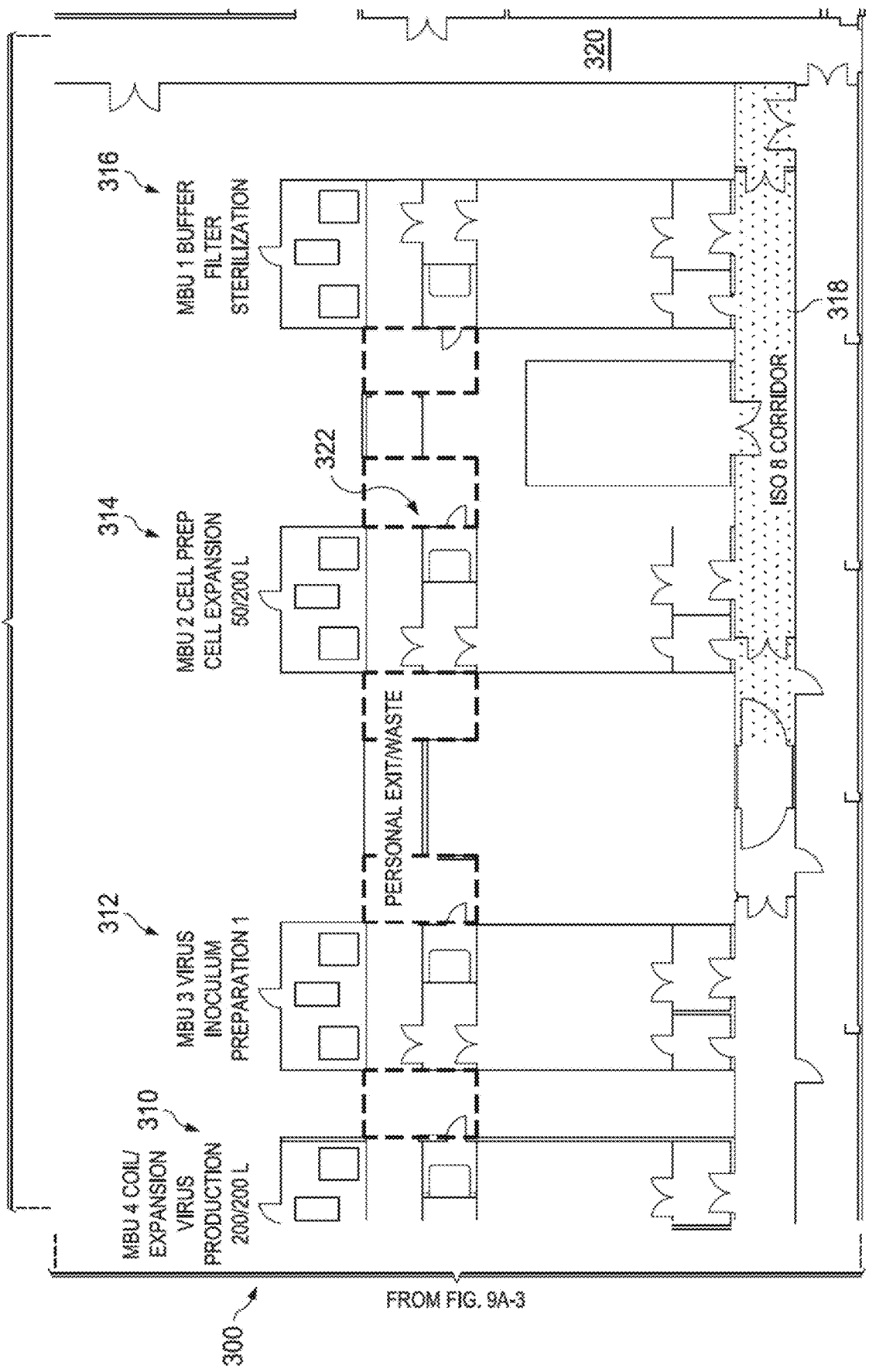

MODULAR, SELF-CONTAINED, MOBILE CLEAN ROOM

CROSS-REFERENCE TO RELATED APPLICATIONS

This application is a divisional application of U.S. patent application Ser. No. 15/727,002, filed Oct. 6, 2017, which is a divisional application of U.S. patent application Ser. No. 13/669,785, filed Nov. 6, 2012, which is a continuation-in-part (CIP) application of U.S. patent application Ser. No. 12/856,888, filed Aug. 16, 2010 (issued Dec. 13, 2016 as U.S. Pat. No. 9,518,748), which claims the benefit of U.S. Provisional Patent Application No. 61/234,302, filed Aug. 16, 2009. The contents of the above applications are hereby incorporated by reference in their entireties for all purposes.

TECHNICAL FIELD OF THE INVENTION

Embodiments of the present invention relate in general to the field of biosafety units, and more particularly, to modular, self-contained, mobile rooms for medical treatments or the manufacture of medical products requiring clean rooms.

STATEMENT OF FEDERALLY FUNDED RESEARCH

None.

BACKGROUND

Without limiting the scope of the invention, its background is described in connection with mobile modular plants.

U.S. Pat. No. 5,656,491, issued to Cassani, et al., teaches a mobile-module plant for the development and the production of biotechnological products on a pilot scale. Briefly, the patent teaches a mobile-module plant for the development and the production of biotechnological products on a pilot scale comprising equipments for the production, separation, purification and finishing of said products and auxiliary equipments, wherein the plant consists of at least two mobile modules suitable for being connected together and integrated one with the other. Each of the mobile modules comprises a movable container. At least one of the movable containers is provided with a preselected own set of said equipments. At least one of the movable containers is aseptic.

BRIEF SUMMARY

In one embodiment, the present invention includes a unitary structure validatable for pharmaceutical manufacturing comprising: at least one controlled air, sealable, sterilizable cleanroom; a mechanical system room adjacent to but separate from the cleanroom comprising: one or more air handling units that provide conditioned air to the cleanroom; and one or more power busses that provide power to electrical outlets in the cleanroom from two sources, wherein at least two power supplies are connectable to one or more external electrical power sources; an integrated fire suppression system integral to the cleanroom; and one or more corridor connectors, wherein a corridor can be attached at the corridor connector. In one aspect, the cleanroom may further comprise a unitary, information technology system that connects to an intranet, an extranet or both, wherein the system connects to and reports from ad/or controls one or more sensors in at least one or more cleanrooms and, if connected, to one or more corridors. The unitary, information technology system can manage each unit, and/or the corridor that connects the units of both. In one aspect, the cleanroom may further comprise one or more external controls connected to one or more sensors that monitor temperature, humidity, air pressure, equipment status, security, fire protection, chemical or biological contamination, hard-wired internet connection or wireless connections connected to an information technology system. In one aspect, the cleanroom may further comprise universal connectors including at least one of an electrical, water, wastewater, gas, HVAC, water, air filtration inputs/outputs or the fire suppression system. In one aspect, the fire suppression system comprises a gas fire suppression system. By integrating the fire suppression/safety system, the cleanroom allows connection/disconnection to host building utilities without a sprinkler attachment, therefore requiring no integration into the host facility fire suppression/sprinkler system or fire marshall approval and/or tests for every connection, disconnection, modification, upgrade, etc. In one aspect, the cleanroom further comprises at least one of an integrated autoclave, a robot or machine capable of cleaning the cleanroom, or a vapor hydrogen peroxide cleaning system. The ability to sterilize the cleanroom and/or corridor unit is a distinct advantage when cleaning and/or converting between different products. Furthermore, placing a dispensing robot or machine into the cleanroom allows for different sterilization protocols, automation in case of highly hazardous materials, and ease of use. Also, integration of the cleanrooms and their utilities allows the user to recirculate that solution through the cleanroom's HVAC at programmed intervals to ensure that the proper cleaning protocol has been achieved. This is particularly useful for gas-based, vapor-based or nebulized sterilization protocols and system, which form part of the present invention. Use of gas, vapor, or nebulized solution has the advantage of assisting in sterilization of all surfaces and any crevices or openings. Additional advantages of the present invention include, having the ability to have an autoclave in each unit that is pre-engineered and does not require additional utility connections. The integrated corridor does not require, but can include, additional HVAC, power, plumbing, electrical and other support functions for the cleanroom operations. Furthermore, the cleanrooms can directly integrate with the corridors to allow unidirectional flow of materials if needed. For example, materials can enter through the front doors and leave through the rear doors of the cleanroom and/or the corridor. In certain embodiments two or more units can be designed to be adjacent and a larger door can be positioned to traverse across the width of the units, including completely across an entire unit and into units on either side of the central unit. The units may also open into a gown-in and gown-out area.

In one embodiment, the present invention includes the ability to be rapidly deployed for a patient care facility comprising: one or more controlled air, sealable, sterilizable cleanrooms having a length and a width; at least one air handling unit in a support room adjacent to the cleanrooms that provide conditioned air to the cleanrooms; and one or more power supplies that provide redundant power to electrical outlets in the cleanroom, wherein the at least two power supplies are connectable to one or more external power sources and the structure; an integrated fire suppression system integral to the cleanroom; and one or more corridor connectors, wherein a corridor can be attached at the corridor connector, wherein at least two cleanrooms are positioned and connected along their width to form at least a double-wide cleanroom, or a combination of connections at the width and length. In one aspect, the cleanroom may further comprise a unitary, information technology system that connects to an intranet, an extranet or both, wherein the system connects to and controls one or more sensors in the at least one or more cleanrooms and if connected one or more corridors. In one aspect, the cleanroom may further comprise one or more external controls connected to one or more sensors that monitor, temperature, humidity, air pressure, equipment status, security, fire protection, chemical or biological contamination, hard wired internet connection or wireless connections connected to an information technology system. In one aspect, the cleanroom may further comprise one or more universal connectors including at least one of an electrical, water, wastewater, gas, HVAC, water, air filtration inputs/outputs or the fire suppression system. In one aspect, the fire suppression system comprises a gas fire suppression system. In one aspect, the cleanroom may further comprise at least one of an integral autoclave, a robot capable of cleaning the cleanroom, a gown-in and gown-out area, or a vapor hydrogen peroxide cleaning system.

In one embodiment, the present invention includes a cleanroom connector or hallway unit or hallway unit adapted to connect to the one or more corridor connectors. In one aspect, the connector or hallway unit is able to be validated for compliance with the requirements of the applicable regulatory agenc(ies). In one aspect, the corridor unit is validated and further comprises a sealed envelope following validation for cGMP manufacturing. In one aspect, the connector or hallway unit may further comprise connection to an information technology system that connects to an intranet, an extranet or both, wherein the system connects to and controls one or more sensors in the unit, one or more external controls connected to one or more sensor that monitor, temperature, humidity, air pressure, equipment status, security, chemical or biological contamination, hard wired internet connection or wireless connection, and optionally at least one of an electrical, water, wastewater, gas, HVAC, water or air filtration inputs/outputs, or a fire suppression system.

In another embodiment, the present invention includes method of making a unitary module or unit able to be validated comprising: building an unitary structure able to be validated for pharmaceutical manufacturing comprising: at least one controlled air, sealable, sterilizable cleanroom; a mechanical system room adjacent to the cleanroom comprising: one or more air handling units in a support room adjacent the cleanroom that provide air to the cleanroom; and one or more power busses that provide power to electrical outlets in the cleanroom from two sources, wherein the at least two power supplies are connectable to one or more external electrical power sources; an integrated fire suppression system integral to the cleanroom; and one or more corridor connectors, wherein a corridor can be attached at the corridor connector. In one aspect, the cleanroom may further comprise the step of pre-validating the unit by an applicable regulatory agency. In one aspect, the cleanroom may further comprise the step of validating the unit and surrounding the unit with a sealed envelope following validation for cGMP manufacturing. In one aspect, the cleanroom may further comprise a unitary, information technology system that connects to an intranet, an extranet or both, wherein the system connects to and controls one or more sensors in the at least one or more cleanrooms and if connected one or more corridors. In one aspect, the cleanroom may further comprise one or more external controls connected to one or more sensors that monitor, temperature, humidity, air pressure, equipment status, security, fire protection, chemical or biological contamination, hard wired internet connection or wireless connections connected to an information technology system. In one aspect, the cleanroom may further comprise one or more universal connectors including at least one of an electrical, water, wastewater, gas, HVAC, water, air filtration inputs/outputs or the fire suppression system. In one aspect, the fire suppression system comprises a gas fire suppression system. In one aspect, cleanroom further comprises at least one of an integral autoclave, a robot capable of cleaning the cleanroom, or a vapor hydrogen peroxide cleaning system.

In yet another embodiment, the present invention includes a method of connecting one more unitary pre-validatable cleanrooms unit comprising: building an unitary structure validatable for pharmaceutical manufacturing comprising: at least one controlled air, sealable, sterilizable cleanroom; a mechanical system room adjacent to the cleanroom comprising: one or more air handling units in a support room adjacent the cleanroom that provide air to the cleanroom; and one or more power busses that provide power to electrical outlets in the cleanroom from two sources, wherein the at least two power supplies are connectable to one or more external electrical power sources; an integrated fire suppression system integral to the cleanroom; one or more corridor connectors, wherein a corridor can be attached at the corridor connector; and a cleanroom connector or hallway unit adapted to connect to the one or more corridor connectors. In one aspect, the connector or hallway unit is pre-validated or validated for compliance with the requirements of an applicable regulatory agency. In one aspect, the connector or hallway unit is validated and further comprises a sealed envelope following validation for cGMP manufacturing. In one aspect, the cleanroom may further comprise a connection to an information technology system that connects to an intranet, an extranet or both, wherein the system connects to and controls one or more sensors in the unit, one or more external controls connected to one or more sensor that monitor, temperature, humidity, air pressure, equipment status, security, chemical or biological contamination, hard wired internet connection or wireless connection, and optionally at least one of an electrical, water, wastewater, gas, HVAC, water or air filtration inputs/outputs, or a fire suppression system.

BRIEF DESCRIPTION OF THE DRAWINGS

For a more complete understanding of the features and advantages of the present invention, reference is now made to the detailed description of the invention along with the accompanying figures and in which:

FIG. 5 illustrates a complete view layout of partial views shown in FIGS. 5-1, 5-2, 5-3, and 5-4. FIG. 5-1 is an upper left partial view. FIG. 5-2 is an upper right partial view. FIG. 5-3 is a lower left partial view. FIG. 5-4 is a lower right partial view. Collectively, the partial views illustrate a top view of a complete, comprehensive manufacturing facility that includes manufacturing, processing, packaging, supplies/storage areas, quality control areas, maintenance, decontamination, controlled corridors, finishing and filling pods, locker rooms, mechanical, electrical and other maintenance areas, with some or all being of a modular;

FIG. 9A-1 is an upper left partial view. FIG. 9A-2 is an upper right partial view. FIG. 9A-3 is a lower left partial view. FIG. 9A-4 is a lower right partial view. Collectively, the partial views of FIG. 9A and FIG. 9B show another processing facility that includes a variety of modular unit(s)/pod(s) for the processing and manufacturing of vaccines or other biological materials.

DETAILED DESCRIPTION

Figure 1:
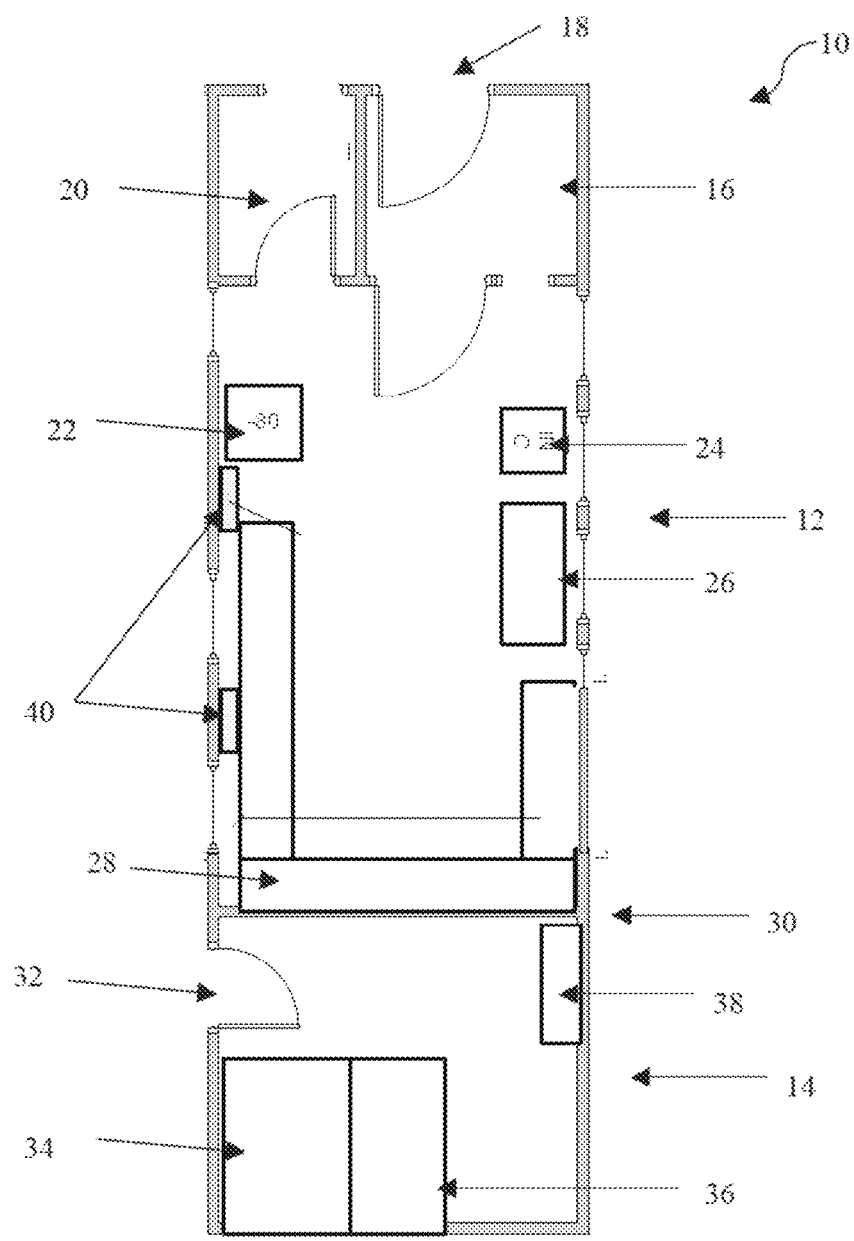
FIG. 1 is a top view of a modular unit of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention includes a modular pharmaceutical facility for the production of, e.g., vaccines and includes all the necessary quality control, quality assurance, and lot release functions. The end product can be made within the same or an adjacent module vaccine filled in bulk vials, suitable for distribution, and compliant with all FDA current Good Manufacturing Practices (cGMP) guidelines. The following terms are used interchangeably "modular unit", "structure", "unit" or "module" to describe a unitary structure that includes at least one portion that is a sealable, working area or cleanroom in which one or more functions or processes are conducted that require a controlled working environment and a mechanical service room or area (which may be closed or open) and that support the clean room and provides redundant services to the cleanroom, e.g., air-handling, electrical, water, waste water, waste disposal, chiller and/or heated water, gas, control units and sensors, security. These services will generally be connected to a source of the service that uses universal connectors, which are those commonly used as fittings in industry (e.g., 110 or 220 volt connections, ½-1 inch liquid or gas connections, wired or wireless connections to an intra, extra or internet and the like).

As used herein the terms "validation" and "pre-validation" are intended to encompass all documented processes or acts undertaken to demonstrate that a procedure, a process or an activity will consistently yield an expected result or outcome. Validation often includes qualification of equipments and systems. Validation is a key required component of Good Manufacturing Practices (GMP) and other regulatory requirements. For example, in the pharmaceutical industry validation of a facility and the process is done prior to obtaining a regulatory approval for the commercial manufacture and sale of the pharmaceutical product. Validation activities in the pharmaceutical industry may also include trial runs (pre-validation) before performing the actual validation to set validation limits, critical manufacturing controls, alert limits, etc and to assess the potential outcome of the actual validation run. Validations routinely performed in the cleaning Validations, process validation, analytical method validation, computer System Validation, qualifying systems and equipment including: design qualification (DQ), component qualification (CQ), installation qualification (IQ), operational qualification (OQ), and process qualification (PQ).

The skilled artisan will recognize that though the structures, facilities or units described in the instant invention are validatable they may not be validated or required to be validated for certain uses and applications, particularly for non-human use or manufacture of products for non-human consumption (for e.g. veterinary applications, agriculture applications, pesticide manufacture, etc.).

Each modular unit, whether operating alone, in a suit or as part of multiple-modular unit facility, can include specific enclosed spaces for the manufacture, fermentation, growth (e.g., in a bioreactor) of the composition requiring an FDA approved, GMP or cGMP facility that includes, e.g., lights, controlled GMP areas consistent with USDA, CDC, FDA or regulations for foreign equivalents, including clean room conditions, purification, chromatography, bulk or individual vial filling, that can be arranged within, e.g., a standard factory or facility with a clearance sufficiently high to accommodate the units within. In one example, the modular units can be placed within a building shell that includes standard electrical connections, water, wastewater, air handling to which the units are connected. The present invention requires no pre-assembly or re-assembly of the multiple units as each can function independently and can be used for multiple purposes.

For example, a complete manufacturing facility can be built, within hours to days, from pre-assembled, pre-approved modular units that include all the equipment necessary for the desired function(s) for that unit within a manufacturing plant. These flexible-by-design GMP modular units allow for the design of production facilities for the rapid deployment and re-deployment of units based on the design needs. For example, one modular unit may include a self-contained bioreactor, the necessary liquid handling devices, refrigerators, tissue culture hoods and microbiology testing equipment, basic laboratory equipment (pipettors, sterile pipette tips, growth media, petri dishes, incubators and other general lab supplies), that has been tested and prevalidated to be compliant with the cGMPs or other regulatory body compliance requirements or in compliance with applicable codes, statutes, ordinances, regulations or equivalents. A modular unit for protein isolation, adjacent to but completely independent from the bioreactor unit, can be positioned and in communication with the bioreactor unit such that the materials manufactured in the bioreactor are rapidly and easily transferred to the protein isolation unit that has, pre-approved and validated protein separation units, e.g., centrifuges, liquid chromatography columns, spectrophotometers, polyacrylamide gel electrophoresis (PAGE) units and bulk packaging units. Next, the bulk protein may be transferred to a packaging unit that includes all the equipment necessary to fill individual doses of the protein, small molecule or other agent that is being manufactured.

Furthermore, the use of individual modules provides for the rapid exchange and continuous manufacture of product in case that one part of the manufacturing process must be changed or revalidated (e.g., in the case of the manufacture of a different biological or the detection of contamination) without the need to re-certify the entire facility. The addition of more modular units also allows for very rapid scale-up that can be customized for short periods of time. For example, a plant can receive the addition of modular units for scaling-up for a short period of time the manufacture and isolation of a vaccine for a short period of time and the redeployment of those units elsewhere upon completion of the production run. In fact, the present invention can be used in existing manufacturing facilities for short-term expansion of manufacturing capacity without the need for revalidation of the new manufacturing capacity or the expensive, long-term installation of an additional production line that will only be used for a short period of time.

The modular units of the present invention can be used as stand-alone facilities (provided they include within all the necessary equipment to manufacture, isolate and package) or may be placed within an existing structure. One example of such a structure is an empty factor or building. One such building could be of standard, pre-cast concrete construction, flat slab with flat, smooth floors, concrete tilt wall, double T precast ceiling and having steel or other walls (which can also be epoxy coated for cleanability). Within with building, the modular units provide the dedicated wet laboratory, growth, bioprocess and purification units necessary for manufacture. These units are simply lifted into position (e.g., pushed on air bearings, casters, pallets), connected to a power source and, if necessary, a water and/or a wastewater supply.

The present invention allows the designer to have the ability to connect one functioning modular unit to one or more additional functioning modules without disrupting the function or compliance of the original modular unit(s). Furthermore, the designer also has the ability to disconnect one functioning module from one or more additional functioning modules without disrupting the function or compliance of the original modular unit(s).

Yet another design option for the modular units of the present invention is the addition of an efficient energy recovery system that allows for energy recapture at a rate much higher than can be expected with existing methods. In this embodiment, the modular unit can also be connected to the central HVAC system of the building that houses the modular units. The intake and exhaust of the redundant HVAC systems of the modular units can be connected to the central HVAC of the building thereby enhancing the energy efficiency of both units. For example, the modular units of the present invention can be placed inside of a second environment (a building with ambient temperature or less humidity), which having the modular unit interact dynamically with that second environment. In this manner of operation, the modular unit can use ambient air that does not need to be treated by a large and expensive external air handling unit.

Another vast improvement over existing designs is the ability of the modular units to service multiple clients with a single cluster of modular units. For example, a biotechnology research park or similar entrepreneurial facility could host various different companies, each having their own production facility or modular unit. One distinct advantage of using the modular units is that each completely self contained modular unit can contain an individual hazardous waste, spills, etc., without affecting any other structures (within a process flow or affecting an adjacent production facility, e.g., when a facility has various manufacturing lines or different companies).

When the modular unit needs to be connected to a source of water, the incoming water could be purified in an adjacent modular unit that could service various different production lines or the module itself could include a water purification unit. The modular unit of the present invention has the advantage that the redundant air handling units, electrical panels and even the water filtration units can be in the portion of the modular unit that is adjacent the clean room and can be serviced without service personnel having to enter the clean room area. When handling wastewater, the modular include can include sump pumps to eliminate waste. Furthermore, the bag in/bag out filters connected to the air handling units can also be changed without the need to enter the cleanroom area. These externally accessible portions of the buildings, or bays, allow for maintenance and maintenance personnel to service the unit without the need to gown-up and enter the clean room area.

Duplicate processes and equipment for air handling, exhaust, etc., with automatic fault tolerance/failover allows the user, e.g., from an external panel or via the internet, to switch-over from a first system to a second system if sensors within the modular unit sense a problem with a component in the first system or as part of regular maintenance.

Another feature of the modular units of the present invention is the ability to used connection devices that are well-known to maintenance personnel. For example, the modular units can use standard quick connectors for chilled water, electricity, etc. that allow the user to 'hot swap' the modular units externally. One advantage of the present invention is that it can take advantage of existing building infrastructure, e.g., mechanical equipment such as boilers, clean steam generator and compressors that can easily be connected to the units. The building's existing maintenance facilities and personnel serve to maintain services and cGMP equipment and environmental service compliance from outside the modular unit.

The present invention also includes a comprehensive management system that provides for the monitoring and maintenance of the module including electricity, water, fire, security, video, etc. externally.

The modular units of the present invention can be made from, for example, a welded aluminum frame, with an all aluminum wall structure of materials and coatings that are cleanable in the drug production environment and are compliant with the cGMP's as described by the USDA, CDC, FDA or equivalent regulatory agency. Stainless steel fixtures and surfaces may also be used when necessary, but could add more weight to the unit if a weight limit exists. The HVAC system can be divide the suite into four zones: a service hallway that will be a controlled non-classified space, gowning room and de-gowning rooms that will be classified at Class 10,000 (ISO 7) and a processing area that will can be classified at Class 10, 100, 1000, 10,000 or higher depending on the requirement. Within the modular unit, the appropriate pressure cascade of at least 0.035 inches of water column is created by adjusting the inlet and exhaust fan output and adjusting the return air volume in each space. For example, pressure changes are often made between the process area and gowning rooms, and gowning rooms to hallway. Exit air filtration will be provided by a "bag in/bag out" HEPA or ULPA filtration module. Incoming air will be pre-filtered with a series of pleated filters integral to the air handler, which can be changed externally from the clean room. Floors can be, e.g., monolithic epoxy, and ceilings can used non-shed 2×4 ceiling tiles along with the requisite fan powered HEPA filters.

The environment of the modular unit, e.g., within the clean room portion of the modular unit or even the maintenance portion of the modular unit, can be controlled and monitored externally using standard network information systems and remote systems monitoring. All instrumentation and process equipment, where appropriate, will also have data interfaces installed on-site and remote data collection and will be internet protocol (IP) addressable.

The modular units will be equipped to easily interface with services such as a single electrical hook-up, chilled water supply, external gas supply, compressed air and liquid nitrogen if necessary to the process. Moreover, modular units can be outfitted with air bearings, so that the modular units can be moved easily to other areas to be reconfigured in near real time to support necessary processes and surge capabilities without disturbing ongoing operations.

Each modular unit can be preassembled with a final documentation package that can include: the design, structural, mechanical, electrical and plumbing drawings, system dossiers, installation qualification and operational qualification plan and executed documents, maintenance logs, and pro-forma quality assurance documents including basic standard operating procedures. These may be provided in hard copy, or provided via a display panel within the modular unit or externally (including within the maintenance bay) that is electronic and can include the necessary passcode/password protection. In fact, the entire unit can include safety features such as passcode/password protection to enter the clean room and/or the maintenance bay, the systems within the clean room (e.g., all the equipment within the room, e.g., bioreactors, columns, centrifuges, computers, assembly lines, input/output lines (liquid, solid, gas), electronic connections (including hard-wire and wireless connections), data storage, liquid and sample storage, storage of controlled substances (including safes or storage cages), incubators, refrigerators or freezers, −70° or other low temperature storage and entry or access to laboratory equipment and supplies.

GENERAL: The redundant HVAC system can include two or more 100% redundant air systems, each having an air handler with discharge air damper, exhaust fan with discharge air damper, and/or an electric duct heater. In operation, the HVAC system can include: a Building Automation System (BAS) that can start/stop the HVAC (and other) equipment electronically or mechanically. An air system that can be "ON" continuously (e.g., have instantaneous failover between systems, including a continuously operating "unoccupied" mode). A Lead and Lag systems can be rotated based on need, e.g., weekly or monthly. The air system can include one or more dampers, end switch closes; lag system exhaust fan discharge and air damper controllers; fan discharge switches; valve control and even duct heater controls.

SUPPLY FAN CONTROL: The constant speed supply fans can be operated from within the clean room, remote automatic start/stop switches, and/or a Building Automation System (BAS) to monitor, e.g., fan status. If the Lead supply fan stops for any reason, the Lead air system will be stopped per the air system stop command and, optionally, an auditory, visual, and/or silent alarm.

TEMPERATURE CONTROL: Temperature in the unit can be controlled via the air handling unit and/or a chilled-water (CHW) valve that modulates to control coil leaving air temperature and/or control of the temperature in the clean room, gown or de-gowning room and/or the maintenance room. The system may also include a duct heater that can modulate to control space temperature.

EXHAUST FAN CONTROL: The constant speed exhaust fans will be capable of remote automatic start/stop and can be monitored via the BAS, which monitors fan status. If the fan(s) stop for any reason, the air handling system will be stopped, and an alarm will be sent to the BAS and the redundant unit will immediate begin operating.

CHILLED WATER SYSTEM CONTROL: The chilled water system will be capable of remote automatic start/stop. The chilled water system will be enabled whenever the air-handling unit (AHU) entering air temperature is above the chilled water coil discharge air setpoint temperature. On a system start command, the CHW pump will start and the chiller controls will be enabled; the chiller will start when flow is proved. On a system stop command, the chiller will be disabled, and the pump will continue to run for five minutes and then be stopped. The BAS will monitor pump status. If the pump fails, the chiller will be disabled, and an alarm will be sent to the BAS. The BAS will monitor chiller status and can provide instantaneous fail-over capability by automatically switching to a redundant chiller. If the chiller fails, the pump will be stopped five minutes later, and an alarm will be sent by the BAS.

ADDITIONAL MONITORING POINTS AND SYSTEM ALARMS: Space pressure can be monitored, e.g., the pressure in the cleanroom. If the pressure drops to 0.0" water column (WC) or below, an alarm can be sent to the BAS. A variety of pressure sensors mounted in the modular unit (e.g., one in the corridor, one each in both the gowning rooms and one in the main lab area of the modular unit) can be provided and monitored. When an alarm is sent to the BAS, the system can call pre-programmed emergency telephone numbers and/or communication electronically via text or email.

Additional Points that can be monitored in the modular unit include, e.g., a static pressure blowout sensor in communication with the air handling units (AHU's) For example, the BAS can determine if there is a belt failure in either of the AHU's or EF's by using, e.g., an amp sensor that monitors the change in amp draw on the motor. Another sensor can be a pitot tube in the supply air duct and exhaust air duct that monitors static pressure connected to the BAS. Also, gravity dampers, automatic dampers and damper end switches and the controls can also be connected to and monitored by the BAS.

FIG. 1 shows a modular unit 10 of the present invention. The modular units of the present invention can be made from, for example, a welded aluminum frame, with an all aluminum wall structure of materials and coatings that are cleanable in the drug production environment and are compliant with the cGMP's as described by the USDA, CDC, FDA or equivalent regulatory agency. The modular unit ten includes two parts, a clean room 12 and a maintenance room 14. The clean room 12 includes a gowning room 16, which provides in this example the sole entry point 18 to the clean room 12, and a de-gowning room 20. In this configuration, the clan room 12 includes a −80° C. freezer 22, an incubator 24, a biosafety cabinet 26 and cabinetry 28, which is pre-installed in this configuration of the clean room 12. The −80° C. freezer 22, an incubator 24, a biosafety cabinet 26 and cabinetry 28 can be attached to the walls and floor by pre-installed attachment points that may be positioned throughout the interior of the clean room 12, or may be custom installed. The maintenance room 14 is separated from the clean room 12 by a wall 30 that isolates the clean room 12 from the maintenance room 14. The maintenance room 14 has a single point of entry 32, through which maintenance personnel can attend to the physical plant portions of the modular unit 10 without needing to access the clean room 12. All the wiring, plumbing and air conduits of the modular unit (not depicted), are pre-installed in the walls of the modular unit are sealed such that the clean room 12 is isolated from the environment surrounding the clean room 12. A redundant HVAC system 34 is found in the maintenance room 14 and can include a bag-in/bag-out filtration system 36. Electrical box 38 is found within the maintenance room 14 and can include not only an electrical panel/breaker box for the modular unit 10, but may also include wired and/or wireless communications equipment. In this example, the return air ducts 40 are positioned in the floor of the clean room and return via a sealed duct to the HVAC system 34.

Figure 2:
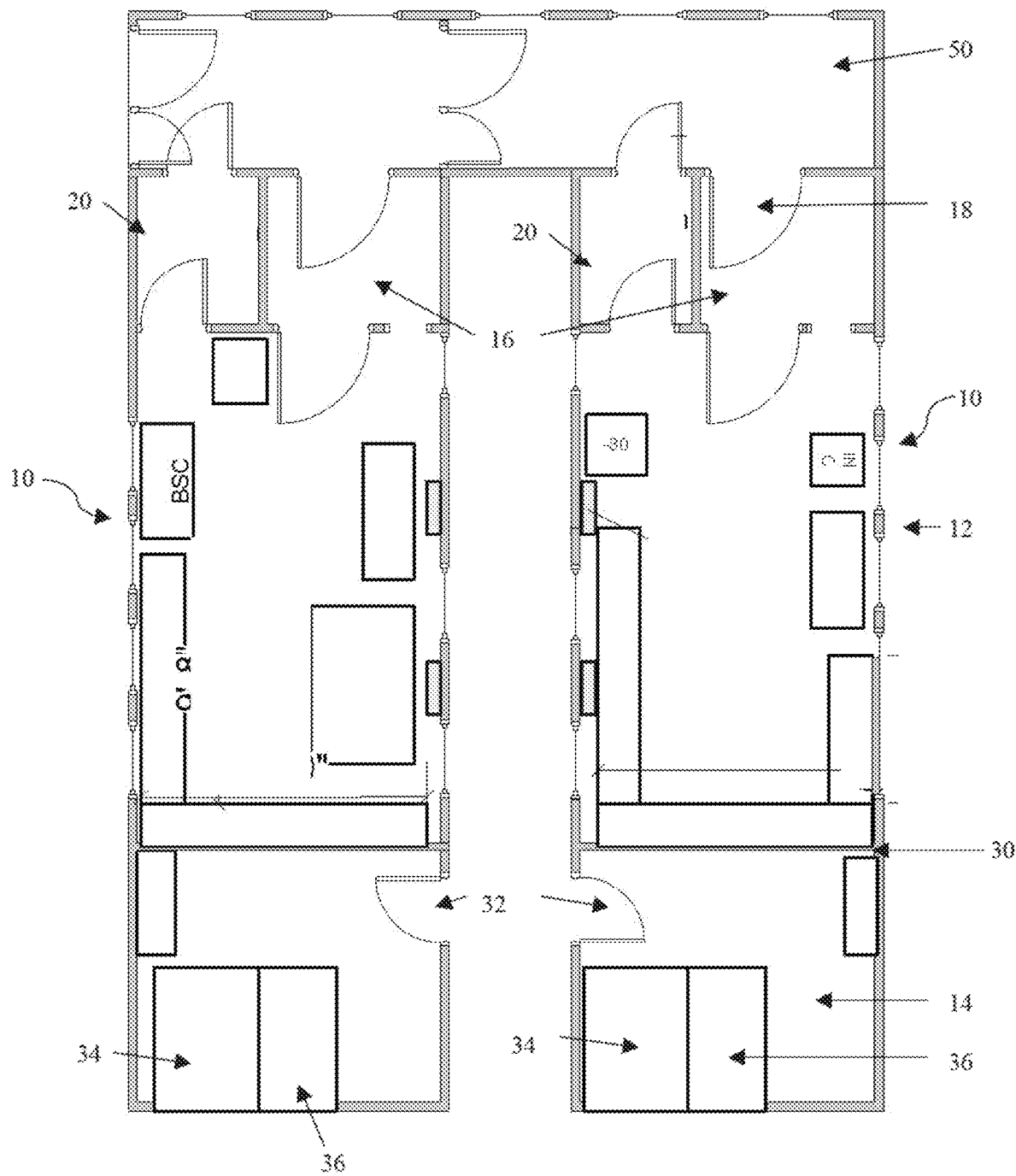
FIG. 2 is a top view of a pair of modular units of the present invention.

In the configuration depicted in FIG. 2, two modular units 10 are shown and can be connected via a service hallway 50, which can be a controlled space, gowning room and de-gowning rooms that will be classified at Class 10,000 (ISO 7) and a processing area that will can be classified at Class 10, 100, 1000, 10,000 or higher depending on the requirement.

Figure 3:
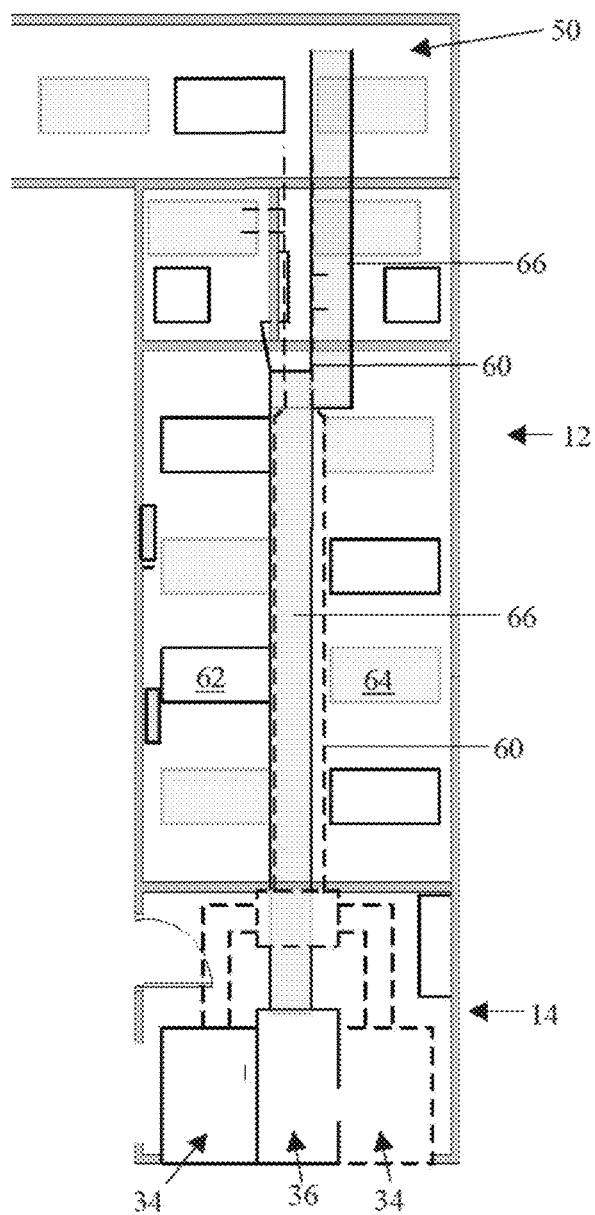
FIG. 3 is a top view of another pair of modular units of the present invention.
Figure 4:
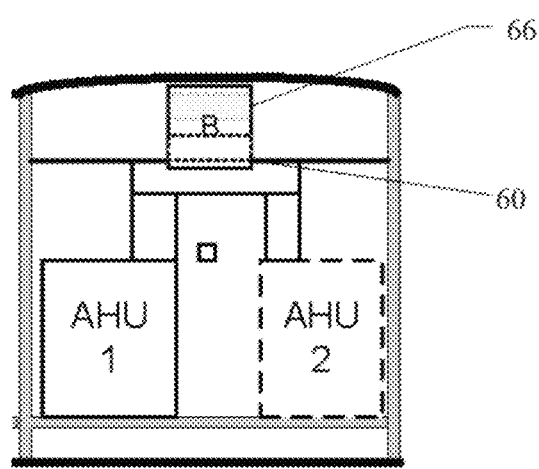
FIG. 4 is a side view of a modular unit of the present invention.
Figure 6:
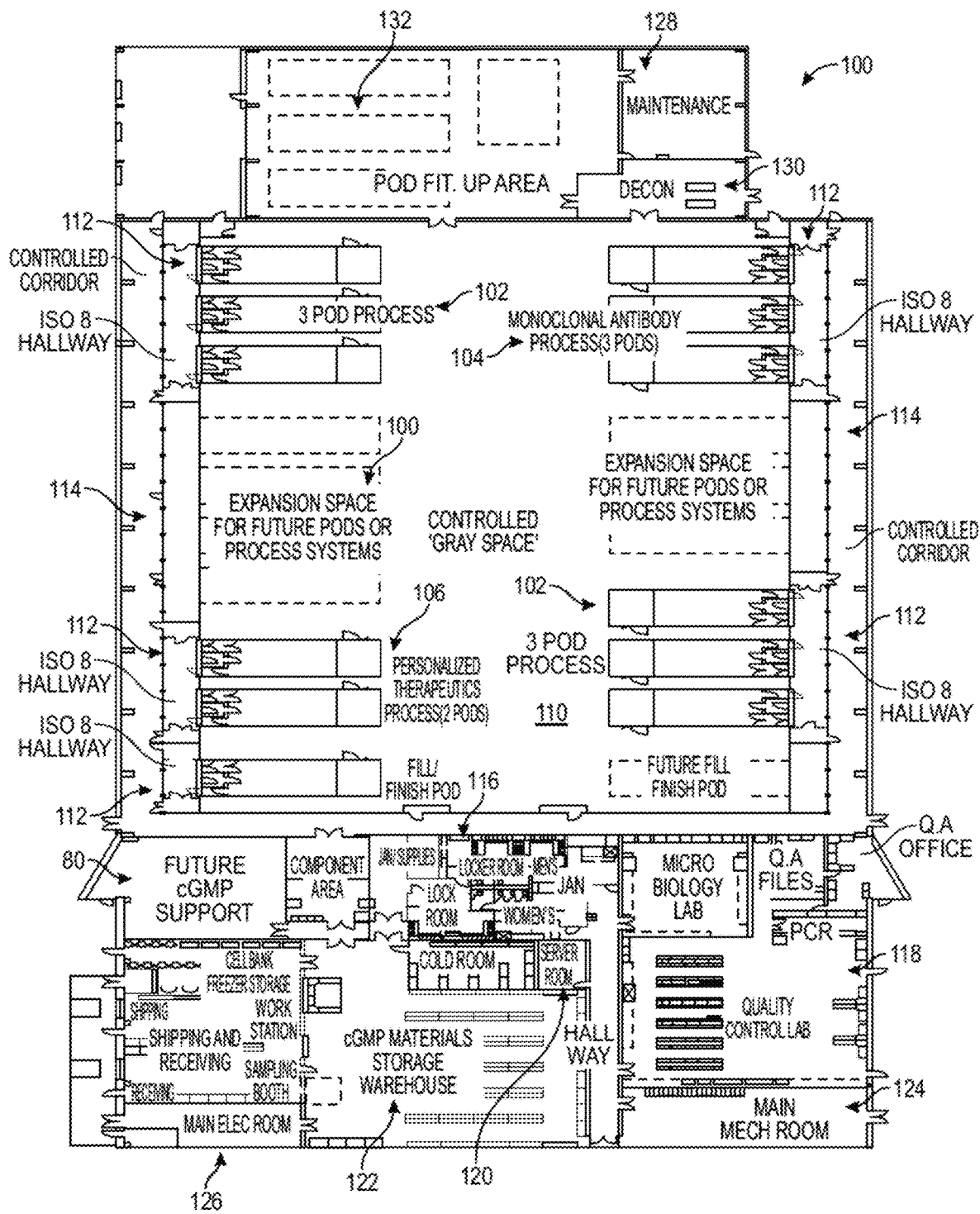
FIG. 6 is another top view of a complete, comprehensive biotherapeutics manufacturing facility that includes manufacturing, processing, packaging, supplies/storage areas, quality control areas, maintenance, decontamination, controlled corridors, finishing and filling pods, locker rooms, mechanical, electrical and other maintenance areas, with some or all being of a modular.
Figure 7:
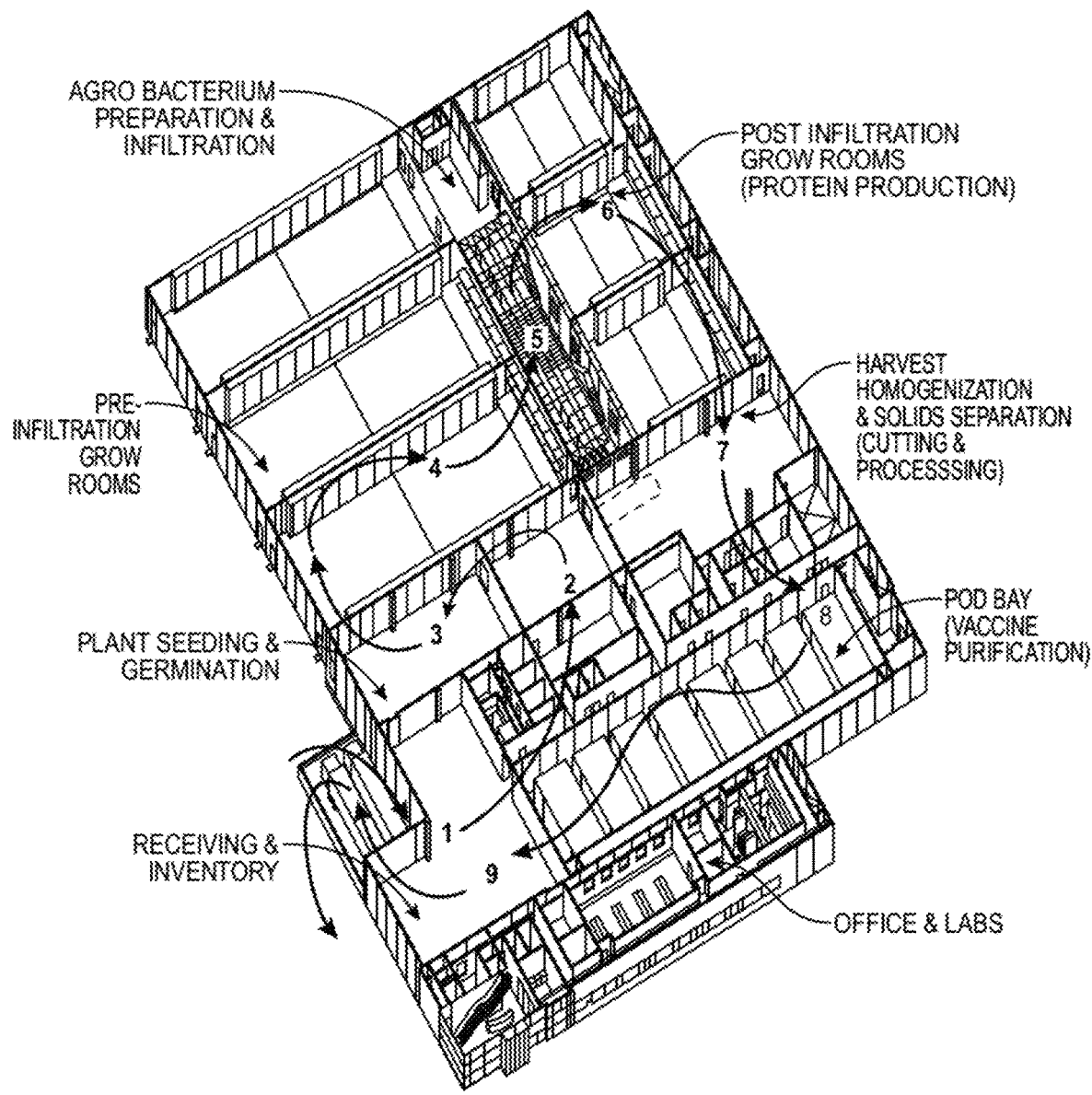
FIG. 7 is a top view of a combination processing facility that include one or more of the modular units of the present invention that includes various components in working communication and that shows an example process flow.

FIG. 3 shows two modular units 10, with a service hallway 50 and the details of an air conduit and filtration system connected to the air handling units 60. Within the modular unit 10, the appropriate pressure cascade of at least 0.035 inches of water column is created within the conduits 60 by the use of changes in conduit size and/or baffles and return ducts 66. For example, pressure changes are often made between the process area and gowning room 16, and de-gowning room 20 to hallway 50. Exit filtration will be provided by a "bag in/bag out" HEPA or ULPA filtration 36, and HEPA filters 62, which alternate with lighting fixtures 64. Incoming air may be pre-filtered with a series of pleated filters integral to the air handler system 24, which can be changed externally from the clean room 12. Floors can be, e.g., monolithic epoxy, and ceilings can used non-shed 2×4 ceiling tiles along with the requisite fan powered HEPA filters. FIG. 4 shows a side view in which the conduits 60 are shown in relation to return ducts 66.

The present invention includes one or more of the following sensors and, optionally, electronic reporting units that report, in real-time or based on a pre-determined or programmable schedule, wherein the sensors can report on the status of the various areas or systems of the modular units, including: Room temperature (degrees C. or F); Room relative humidity; Four Pressure sensors (e.g., 1 in the corridor, 1 in gown-in area, 1 in gown-out area, 1 in lab/cleanroom); Ambient air temperature (degrees C. or F); Ambient relative humidity; HEPA filter lifecycle status (e.g., measured in inches e.g.); Chilled water temperature (degrees C. or F); Chilled water pressure (psi); Supply fan status (2 each); Exhaust fan status (2 each); Chilled water status (degrees C. or F); Chilled water supply and return temperature (degrees C. or F); Chilled water pump status or various sensors to read status and performance on: temperature, $CO_2$, airflow, off/on, security, door position, personnel entry and exit, inventory control.

Hardened for harsh environments: The structure and portability of the cleanrooms provide for use as a facility hardened for harsh environments. As described previously herein the cleanroom can be used as a stand-alone unit or can be combined with other modules that may serve as support units, such as a unit to contain chiller equipment, and/or a unit to contain mechanical equipment (such as a generator set, a compressor, and/or water containment and or purification equipment). Such a cleanroom or set of cleanrooms can be shipped into an area via various means, such as C17 airforce transport, truck, or boat with the intent of quick set up of a cleanroom facility in an area that has no infrastructure for such. A set-up like this could also be quickly dismantled and removed.

Hospital/Surgical/Triage: The structure, portability, and controlled environment of the cleanrooms provides for use as a hospital unit or units, surgical suite or suites, and/or triage facilities for areas in which there is otherwise no available infrastructure for such facilities or in areas in which such facilities have been recently destroyed, or in areas in which additional facilities are required before one can be constructed. The controllability of the interior environment and ability to create a Class 100 or Class 1000 compliant environment would be suitable for a burn unit, where patients are at particular risk for infection from exposure to airborne microbes.

Massively portable: The units described herein are compact enough to be transported via various modes, including but not limited to road, train, sea, and air. Units may be placed on a flatbed trailer pulled by a semi, sealed in shipping containers for rail or sea transport, or placed upon an air carrier, such as a Boeing C-17 Globemaster III military transport plane. Units are designed and engineered to withstand the physical stress of travel via road, train, sea, and air and are of a weight such as to be portable via these transportation means. The units of the present invention can also be built with structural lifting points and lifted via hydraulic lifts inserted into these points to be raised to slightly above the level of a flat-bed trailer. The flat-bed trailer is then backed under the unit and lowered and secured for transport.

Designed for maximal cleanability: As cleanability is crucial for the aseptic environment provided by the cleanrooms, floors, windows, and walls are made in such a way as to reduce, if not completely eliminate, cracks, crevices, joint spaces and other areas in which dust and microbes may rest or accumulate. Windows are flush-mounted to the interior to reduce small areas in which dust and microbes may accumulate and to increase to ease of cleaning of the joint at which a window meets a wall. Floors are covered with a monolithic application of an epoxy resin. Walls are likewise covered with a monolithic application of an epoxy resin. This creates increased cleanability of both wall and floor surfaces, but more importantly, reduces joint and cracks within both the wall and floor surfaces themselves, as well as eliminating a joint and or crack where wall meets floor.

Cleanrooms are constructed in multiple dimensions, including 12 feet by 43 feet, 15 feet by 43 feet, and 18 feet by 43 feet. Height may be from 10 feet to 18 feet. Lengths may be adjusted as required below 43 feet. These dimensions allow for ultimate flexibility in both use and transport. 12-foot-wide units are most applicable for air and sea transport, while road transport allows for up to 18 feet in width. Height may be increased to 18 feet to allow for the installation of larger equipment, such as large bioreactors that require such headroom.

The cleanrooms of the present invention can be made with monolithic epoxy walls and floors. This provides a very rugged surface and highly cleanable surface for use in Biological Safety Level 3 (BSL3) and Animal Biosafety Level 3 (ABSL3). The clean rooms can be operated in a negative pressure totally isolated mode and when connected to a modular clean hallway. This fact provides at least 3 levels of air cascade essential in BSL3 applications. A new approach has also been designed by the present inventors for an ABSL3 facility that uses the portability of the clean rooms to maximum advantage and a new paradigm. The design is depicted in FIGS. 5-1, 5-2, 5-3, and 5-4. The concept is that the animals stay in one place and that services and procedures are brought to them by movable clean rooms. The outer row of cleanrooms represents areas for animals being treated in separate studies.

Services like food supply and waste removal can be facilitated by movable clean rooms. Experimental support services like imaging, surgery, necropsy and others can be brought to the individual experimental animal containment area. The animals can be transferred in containment to the service required and returned if applicable to their habitat clean rooms. This approach allows superior containment for these processes since the animals will not be transported throughout a building to different laboratories for treatment or sophisticated diagnostic and other procedures. Containment is facilitated by a docking system that provides a contained pass through for animals. The pressure can be maintained negatively for both cleanrooms in relation to the gray space. Both clean rooms are isolated from the gray space by filtration on both inlet and exhaust air.

The clean rooms can be used as manufacturing or medical facilities for the military and others by being constructed for air transports on cargo planes such as the C-17 military transport. Factories configured by multiple modules can be transported and enable quickly with self-contained power, steam and chilled water service modules. Other anticipated uses are for medical and surgical treatment suites in remote areas.

Figure 8:
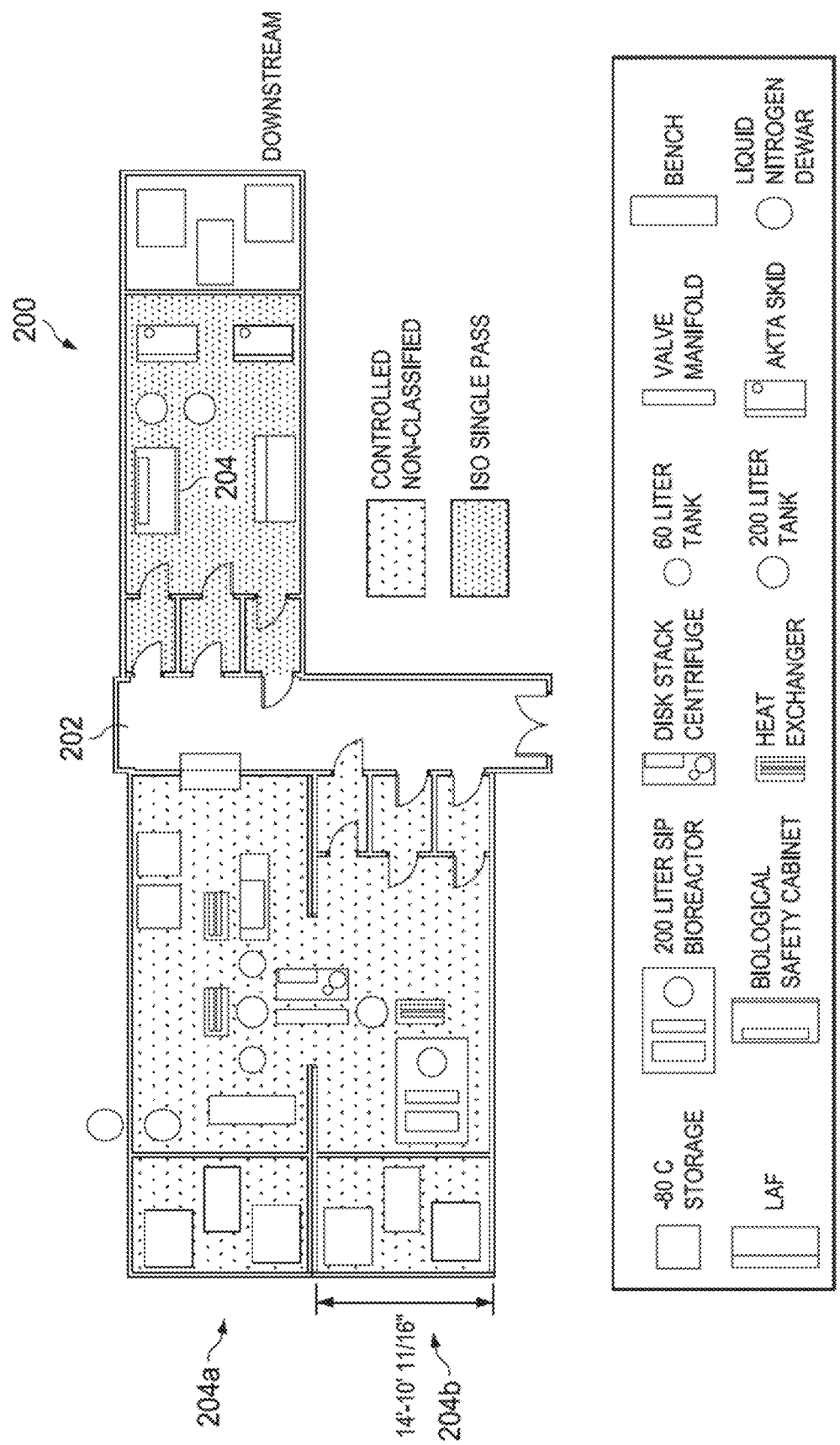
FIG. 8 is another top view of a combination processing facility with a common corridor.

Filling of antigens at the site of a bioterrorism or biological "hot zone": A mobile clean room can be designed with a sterile filling machine to fill injector tips that are used for air powered injection. This indicates that a clean room could be airlifted to a site of an event and that bulk pharmaceutical substance could be delivered directly from the manufacturer to the site in bulk fill containers containing hundreds of thousands of doses, e.g. 250 ml and 1 mg per ml per ml would yield 2500 doses at 100 micrograms per dose at a dose size of 0.1 ml. The fact that the bulk material could be delivered to the site with no need to fill into individual doses. This could save weeks in the delivery to a "hot zone" since an intermediate fill step would not have to be done.

A specially designed chamber will allow the transfer of waste from the clean room to a sealed portable container for transport of solid and liquid wastes from a process. This container is portable and docks with a dedicated pass through to transfer waste materials. The outer door of the pass through is then closed followed by the inner door on the clean room and the transfer is complete.

The clean rooms of the present invention have been included in a new concept involving up to eight different manufacturing processes can be done in the same gray space infrastructure as depicted in FIGS. 5 and 6. Because of the containment and flexibility multiple processes can be implemented and changed without disturbing other stakeholders in the space.

FIGS. 5-1, 5-2, 5-3, and 5-4 collectively are a top view of a complete, comprehensive manufacturing facility 70 that includes manufacturing, processing, packaging, supplies/storage areas, quality control areas, maintenance, decontamination, controlled corridors, finishing and filling pods, locker rooms, mechanical, electrical and other maintenance areas, with some or all being of a modular. The numbered units 1-8 are modular in nature and are shown connected to modular gown-in-gown-out or other like interface areas 72 (e.g., decontamination) that then connect to corridors 74 that can be part of an existing facility or can themselves be modular. Each of the numbered modules 1 to 8 can be connected to other modular units, e.g., an imaging unit 76, surgery/necropsy unit 78, supplies 80, waste 82, water 84, or other modules that can be plugged into the numbered modules based on the design needs for the manufacturing facility 70. Other support areas can be connected to the same that provide office space, restrooms, etc.

FIG. 6 is another top view of a complete, comprehensive biotherapeutics manufacturing facility 100 that includes manufacturing, processing, packaging, supplies/storage areas, quality control areas, maintenance, decontamination, controlled corridors, finishing and filling pods, locker rooms, mechanical, electrical and other maintenance areas, with some or all being of a modular. The various modular units or pods can include, e.g., general basic pod(s) 102, monoclonal antibody pod(s) 104, personalized therapeutic pod(s) units, expansion areas in a controlled "gray" space 110. The units or pod(s) 102, 104, 106, can be connected to one or more modular hallways, e.g., ISO certified hallways 112 and secondary hallways 114, which are shown connected to a single modular gown-in-gown-out and/or locker rooms 116. Each of the modules or pods can then be connected to modular or permanent office areas, quality control areas (e.g., including microbiology) 118, a server room 120, cGMP or other storage areas 122, mechanical room or pod(s) 124, electrical room or pod(s) 126, general maintenance room or pod(s) 128, decontamination area or pod(s) 130, and even a pod(s) fit-up and decontamination area 132 in which pod(s) can be staged and prepared for installation or cleaned following use. Other support areas can be connected to the same that provide office space, restrooms, etc.

FIG. 7 is a top view of a combination processing facility that include one or more of the modular units or pods of the present invention that includes various components in working communication and that shows an example process flow. A receiving and inventor area/pod at step 1 and 9 is shown. The materials are prepared and transferred to a plant seeding and germination area(s)/pod(s) at step 2 and 3, followed by pre-infiltration and grow room(s)/pod(s) at step 4. After the plants are grown in step 4, the processed materials enter, e.g., an agrobacterium preparation and infiltration area(s)/pod(s) at step 5. At step 6, the plants are processed post-infiltration and the plants are grown for, e.g., protein production in the production area(s)/pod(s). At step 7, the plants enter unit(s)/pod(s) used for harvesting, e.g., by homogenization and the solids are separated (cutting and processing). At step 8, the unit(s)/pod(s)pod are used in, e.g., vaccine isolation, purification, filtration, processing, and/or packaging. An adjacent unit or pod can include office, restrooms, lockers, and/or lab space.

FIG. 8 is another top view of a combination processing facility 200 with a common corridor 202, single pod 204 or double pods 204a/204b.

Figures 1, 9A:
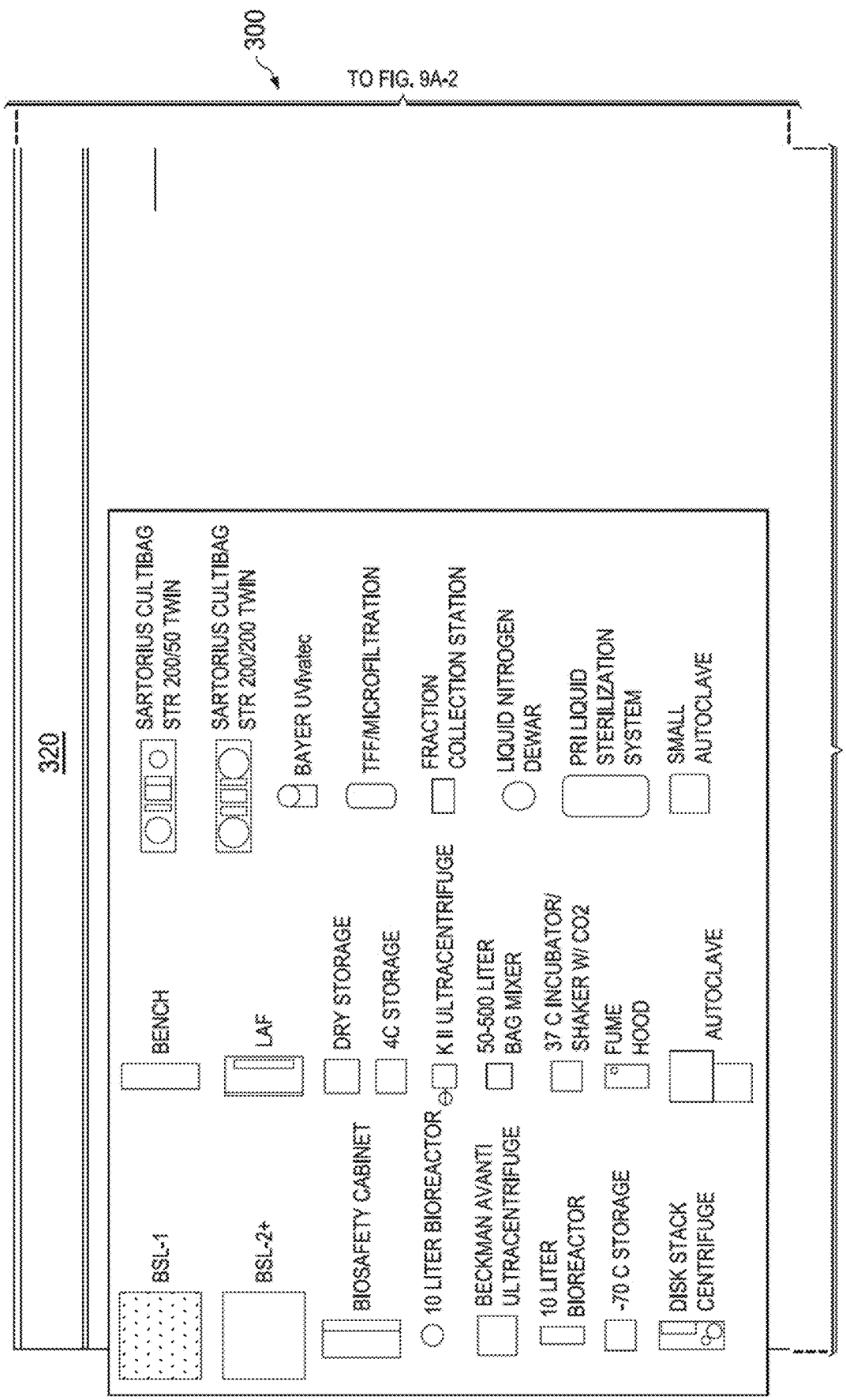
FIG. 9A illustrates a complete view layout of partial views shown in FIGS. 9A-1, 9A-2, 9A-3, and 9A-4.
Figure 9B:
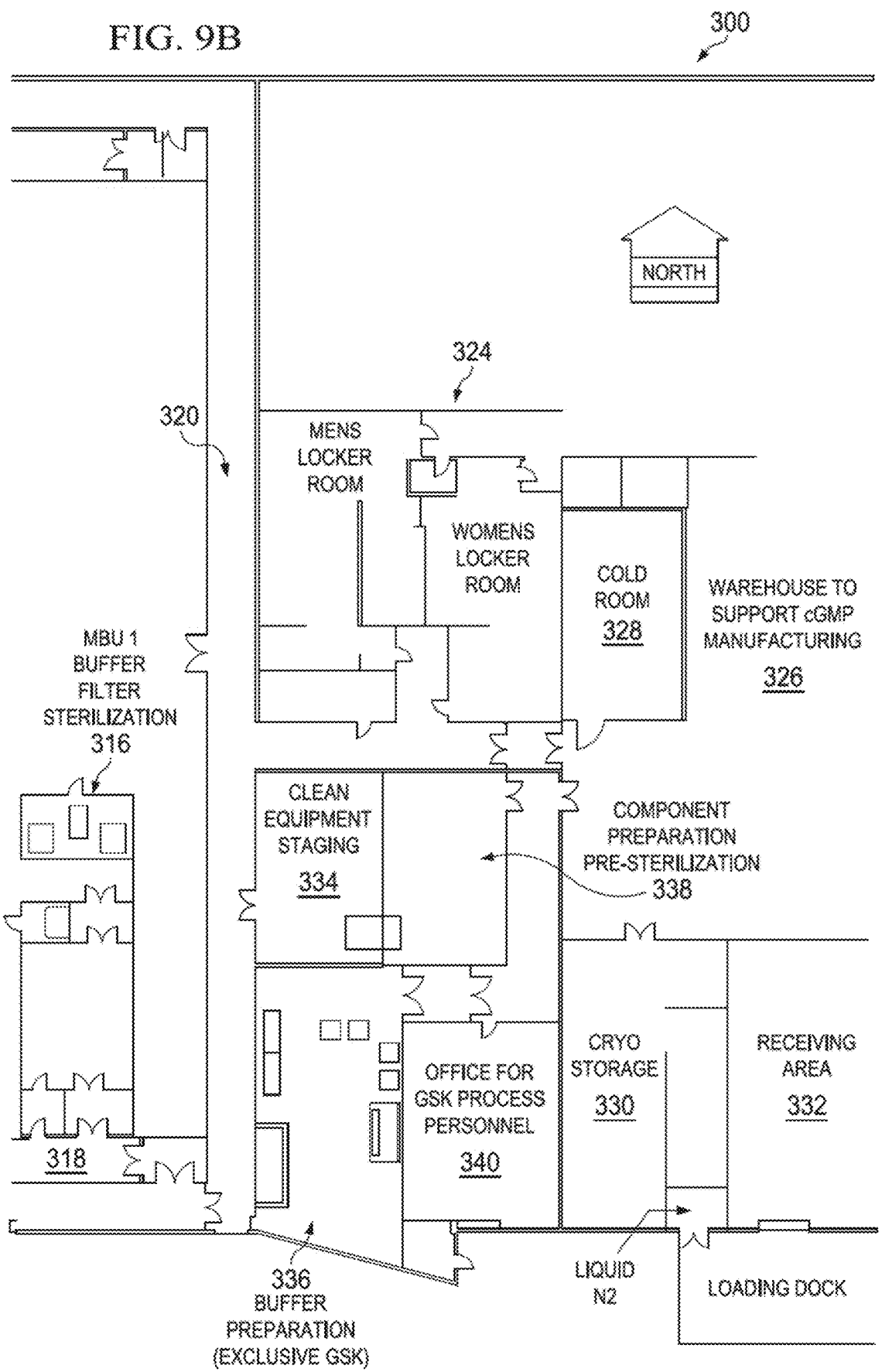

FIGS. 9A-1, 9A-2, 9A-3, 9A-4, and 9B show another processing facility 300, that includes a variety of modular unit(s)/pod(s) for the processing and manufacturing of, e.g., vaccines or other biological materials. The various unit modular unit(s)/pod(s) may include: processing and bulk filling unit 302, wash and waste processing and treatment 304, ultracentrifugation and filtering 306, centrifugation and inactivation 308, expansion and viral production 310, virus inoculum and preparation 312, cellular preparation and expansion 314 and even a material filtration and sterilization 316. These various modular unit(s)/pod(s) 302-316 may include more of the individual units if additional capacity is required (e.g., units 322). The various modular unit(s)/pod(s) 302-316 are shown connected by one or more modular corridor(s) 318, which may be isolation corridors that comply with, e.g., ISO 8 air filtration capabilities, which may then connect to regular corridors 320. On the opposite end from the various modular unit(s)/pod(s) 302-316 is shown a second corridor 322, which may be used for, e.g., waste transport and/or as a personnel exit. The various modular unit(s)/pod(s) 302-316 are shown, in this example, to have autoclaves, and may also include benches, biosafety cabinets, dry storage, wet storage, freezers, (e.g., −70 degree freezer(s)), bioreactors, incubators, fume hoods, tangential flow filtration units, other filtration units, HPLCs, FPLCs, fraction collection stations, liquid sterilization systems, liquid nitrogen or other gases, and incubators/shakers. FIG. 9B shows the continuation of the processing facility 300 connected by corridor 320 (also shown are material filtration and sterilization 316 and modular corridor(s) 318). Corridor 320 can lead to one or more common work areas, including staff locker rooms 324, warehouse areas 326, cold room storage 328, cryostorage 330, receiving area(s) 332, equipment staging area(s) 334, buffer preparation 336, other component preparation 338 and offices 340.

Modular clean rooms are being used for the downstream portion processing in a biologics or a very large commercial vaccine facility. Eight clean rooms were used for downstream processing including tangential flow filtration, chromatography, sterile filling, buffer preparation, equipment washing and quality control testing.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:
1. A rapid deployment cleanroom system comprising:
at least two unitary modular structures, each structure having a length and a width sized for portability by truck, wherein the at least two structures are positioned and connected to form at least a double-wide cleanroom within the structures;

a maintenance room located within an end of one of the at least two structures, the maintenance room isolated from the at least double wide cleanroom;

an air handling unit that provides air to the at least double-wide cleanroom or a power supply that provides power to electrical outlets in the at least double-wide cleanroom, the air handling unit or the power supply located in the maintenance room; and a corridor from which the at least two structures project such that the maintenance room located within an end of the at least two structures is on an opposite end of the at least double-wide cleanroom from the corridor.

2. The system of claim 1, further comprising:
a unitary, information technology system that connects to an intranet, an extranet, or both, wherein the information technology system is configured to connect to and control one or more sensors in the at least double-wide cleanroom.

3. The system of claim 1, further comprising:
one or more external controls configured to connect to one or more sensors that monitor, temperature, humidity, air pressure, equipment status, security, fire protection, chemical or biological contamination, hard wired internet connection or wireless connections connected to an information technology system.

4. The system of claim 1, further comprising:
universal connectors including at least one of an electrical, water, wastewater, gas, HVAC, water, air filtration inputs/outputs or a fire suppression system.

5. The system of claim 1, wherein the at least double-wide cleanroom further comprises at least one of an integral autoclave.

6. The system of claim 1, wherein the corridor further comprises a connection to an information technology system that connects to an intranet, an extranet, or both, wherein the information technology system is configured to connect to and control one or more sensors in the rapid deployment cleanroom system, one or more external controls connected to one or more sensors that monitor, temperature, humidity, air pressure, equipment status, security, chemical or biological contamination, hard wired internet connection or wireless connections, and optionally at least one of an electrical, water, wastewater, gas, HVAC, water or air filtration inputs/outputs, or a fire suppression system.

7. The system of claim 1, further comprising:
a gowning room between the at least double-wide cleanroom and the corridor, the cleanroom having an entry point for personnel from the corridor through the gowning room, the gowning room configured to have a pressure differential between the gowning room, the cleanroom, and the corridor.

8. The system of claim 1, wherein the at least one air handling unit comprises at least two air handling units configured such that if any of the air handing units fail during operation of the cleanroom, each of the at least two air handling units has instantaneous fail-over of air to the cleanroom.

9. The system of claim 1, wherein the at least one power supply comprises at least two power supplies configured such that if any of the power supplies fail during operation of the cleanroom, each of the at least two power supplies has instantaneous fail-over without loss of power to the cleanroom.

10. The system of claim 1, further comprising:
an entrance to the mechanical room for personnel configured to allow the maintenance room to be serviced without entering the at least double-wide cleanroom or the corridor.

11. The system of claim 1, further comprising:
air bearings under each of the unitary modular structures.

12. The system of claim 11, wherein the structures reside on flat, smooth floors, wherein the air bearings permit movement of the structures.

* * * * *